United States Patent [19]
Chiang

[11] Patent Number: 5,648,523
[45] Date of Patent: Jul. 15, 1997

[54] FULLERENE DERIVATIVES AS FREE-RADICAL SCAVENGERS

[76] Inventor: Long Y. Chiang, 4F, No. 15, Lane 97, Shin-Shen S. Road, Sec. 1, Taipei, Taiwan

[21] Appl. No.: 547,714

[22] Filed: Oct. 26, 1995

[51] Int. Cl.$^6$ .................................................. C07C 309/01
[52] U.S. Cl. ........................... 562/100; 564/57; 564/123
[58] Field of Search ........................... 562/100; 564/57, 564/123

[56] References Cited

U.S. PATENT DOCUMENTS

| | | |
|---|---|---|
| 5,177,248 | 1/1993 | Chiang et al. ............................. 560/86 |
| 5,294,732 | 3/1994 | Chiang et al. ............................. 560/86 |
| 5,416,188 | 5/1995 | Chiang et al. ............................. 528/291 |

OTHER PUBLICATIONS

Belik et al., "Reaction of Buckminsterfullerene with orth–Quinodimethane: a New Access to Stable $C_{60}$ Derivatives", Angew. Chem. Int. Ed. Engl. 1:78–80, 1993.

Chiang et al., "Efficient Synthesis of Polyhydroxylated Fullerence Derivatives via Hydrolysis of Polycyclosulfated Precursors", J. Org. Chem., 59:3960–3968, 1994.

Chiang et al., "Evidence of Hemiketals Incorporated in the Structure of Fullerols Derived from Aqueous Acid Chemistry", J. Am. Chem. Soc., 115:5453–5457, 1993.

Chiang et al., "Free Radical Scavenging Activity of Water-soluble Fullernols", J. Chem. Soc. Chem. Commun., 1283–1284, 1995.

Chiang et al., "Multi–hydroxy Additions onto $C_{60}$ Fullerene Molecules", J. Chem. Soc. Chem. Commun., 1791–1793, 1992.

Chiang et al., "Versatile Nitronium Chemistry for $C_{60}$ Fullerene Functionalization", J. Am. Chem. Soc., 114:10154–10157, 1992.

Friedman et al., "Inhibition of the HIV–1 Protease by Fullerene Derivatives: Model Building Studies and Experimental Verification", J. Am. Chem. Soc, 115:6506–6509, 1993.

Hirsch et al., "Globe–trotting Hydrogens on the Surface of the Fullerene Compound $C_{60}H_6(N(CH_2CH_2)_2O)_6$", Angew. Chem. Int. Ed. Engl. 30:1309–1310, 1991.

Hoke et al., "Reaction of Fullerenes and Benzyne", J. Org. Chem. 57:5069–5071, 1992.

Isaacs et al., "Improved Purification of $C_{60}$ and Formation of γ and π–Homoaromatic Methano–Bridged Fullerenes by Reaction with Alkyl Diazoacetates", Helvetica Chimica Acta 76:1231–1250, 1993.

Juha et al., "Reactivity of Fullerenes with Chemically Generated Generated Singlet Oxygen", J. Chem. Soc., Chem. Commun., 2437–2438, 1994.

Krusic et al., "Radical Reactions of $C_{60}$", Science 254:1183–1185, 1991.

Li et al., "$C_{60}$ Fullerol Formation Catalysed by Quaternary Ammonium Hydroxides", J. Chem. Soc., Chem. Commun. 1784–1785, 1993.

Paulus et al., "Diethyl Methano–$C_{60}$–fullerene–61, 61–dicarboxylate Chloroform Solvate at 193K, $C_{60}C(CO_2C_2H_5)_2CHI_3$", Acta Cryst, C51:143–146, 1995.

Prato et al., "[3+2] and [4+2] Cycloadditions of $C_{60}$", J. Am. Chem. Soc. 115:1594–1595, 1993.

Shu et al., "Reaction of [80]Fullerene with 1–(4–Methoxyphenyl)–1–(trimethylsilyloxy)ethylene", J. Chem. Commun. 367–368, 1995.

Roy et al., "$NO_2$ Adducts of $C_{60}$: Synthesis of Polynitro–Polyhydroxy Fullerenes", J. Chem. Soc., Chem. Commun., 275–276, 1994.

Schneider et al., "Formation of Fullerols via Hydroboration of Fullerene–$C_{60}$", J. Chem. Soc., Chem. Commun., 463–464, 1994.

Suzuki et al., "Systematic Inflation of Buckminsterfullerene $C_{60}$: Synthesis of Diphenyl Fulleroids $C_{61}$ to $C_{66}$", Science 254:1186–1188, 1991.

Taliani et al., "Light–induced Oxygen Incision of $C_{60}$", J. Chem. Soc. Chem. Commun., 220–222, 1993.

Tokuyama et al., "Photoinduced Biochemical Activity of Fullerene Carboxylic Acid", J. Am. Chem. Soc. 115:7918–7919, 1993.

Tsuda et al, "Addition Reaction of Benzyne to $C_{60}$", Chemistry Letters 2333–2334, 1992.

Wilson et al., "A New Reaction of Fullerenes: [2+2] Photocycloaddition of Enones", J. Am. hem. Soc. 115:8495–8496, 1993.

Balch et al., "Supramolecular Aggregation of ($\pi^2$ –$C_{60}$) Iridium Complex Involving Phenyl Chelation of the Fullerene", J. Am. Chem. Soc. 114:5455–5457, 1992.

Primary Examiner—Joseph Conrad
Attorney, Agent, or Firm—Fish & Richardson P.C.

[57] ABSTRACT

The invention relates to fullerene derivatives which are capable of scavenging free radicals. The derivatives have the formula $F(-X)_m(-Y-Z)_n$, in which F is a fullerene core; each X is independently $-CO_2^-$, $-SO_3^-$, $-SH$, or the like; each $-Y-Z$ is independently $(C_{3-30}$ alkyl ether$)_{50}$—$CH_2$—$CO_2^-$, $(C_{3-30}$ alkyl ester$)_{50}$—$CH_2$—$SO_3^-$, $(C_{3-30}$ alkyl amide$)_{50}$—$CH_2$—$SH$, or the like; m is 0–30; n is 0–30; and the sum of m and n is 2–30.

20 Claims, 2 Drawing Sheets

FULLERENE DERIVATIVES AS FREE-RADICAL SCAVENGERS

BACKGROUND OF THE INVENTION

Conjugated caged olefins, such as $C_{60}$ and analogous molecules thereof, have been found to be extraordinarily susceptible to the attack of a variety of chemical reagents. Particularly, they all exhibit high reactivity toward multiple additions of organic free radicals. This reactivity is, presumably, correlated to the intrinsically large electronegativity of such molecules.

Several functionalized fullerene derivatives have been reported for the biochemical or medical related studies. For example, bis(phenethylamino-succinate)$C_{60}$ inhibited the HIV-1 protease. Friedman, et al., J. Am. Chem. Soc. 1993, 115, 6506. As another example, photoactivated water-compatible monofunctionalized $C_{60}$ showed DNA-cleaving activity and in vitro cytotoxicity against the HeLa S3 cell line. Tokuyama, et al., J. Am. Chem. Soc. 1993, 115, 7918. Both activities were eliminated in the absence of a light source.

SUMMARY OF THE INVENTION

The present invention relates to fullerene derivatives which, like the parent fullerenes, are capable of scavenging free radicals, but have reduced or no biological toxicity.

An aspect of this invention features a group of compounds of the following formula and their counter ionic salts:

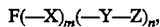

wherein

F is a fullerene core;

each X is independently —$CO_2^-$, —$SO_3^-$, —SH, —$PO_3^-$, —O—$PO_3^{-2}$, —O—PO(O$^-$)—O—$PO_3^{-2}$, —O—PO(O$^-$)—O—PO(O$^-$)—O—$PO_3^{-2}$, or —O—PO(O$^-$)—O—$CH_2$—$CH_2$—$NH_3^+$;

each Y is —A—B—, in which A is independently —$CH_2$—, —O—, —S—, —NH—CO—NH—, or —NH—CO—; and B is independently —$R_a$—O—[Si(CH$_3$)$_2$—O—]$_{1-100}$, $C_{1-2000}$ alkyl (a divalent radical), $C_{6-40}$ aryl (a divalent radical), $C_{7-60}$ alkylaryl (a divalent radical), $C_{7-60}$ arylalkyl (a divalent radical), ($C_{1-30}$ alkyl ether)$_{1-100}$, ($C_{6-40}$ aryl ether)$_{1-100}$, ($C_{7-60}$ alkylaryl ether)$_{1-100}$, ($C_{7-60}$ arylalkyl ether)$_{1-100}$, ($C_{1-30}$ alkyl thioether)$_{1-100}$, ($C_{6-40}$ aryl thioether)$_{1-100}$, ($C_{7-60}$ alkylaryl thioether)$_{1-100}$, ($C_{7-60}$ arylalkyl thioether)$_{1-100}$, ($C_{2-50}$ alkyl ester)$_{1-100}$, ($C_{7-60}$ aryl ester)$_{1-100}$, ($C_{8-70}$ alkylaryl ester)$_{1-100}$, ($C_{8-70}$ arylalkyl ester)$_{1-100}$, —R—CO—O—($C_{1-30}$ alkyl ether)$_{1-100}$, —R—CO—O—($C_{6-40}$ aryl ether)$_{1-100}$, —R—CO—O—($C_{7-60}$ alkylaryl ether)$_{1-100}$, —R—CO—O—($C_{7-60}$ arylalkyl ether)$_{1-100}$, ($C_{4-50}$ alkyl urethane)$_{1-100}$, ($C_{14-60}$ aryl urethane)$_{1-100}$, ($C_{10-80}$ alkylaryl urethane)$_{1-100}$, ($C_{10-80}$ arylalkyl urethane)$_{1-100}$, ($C_{5-50}$ alkyl urea)$_{1-100}$, ($C_{14-60}$ aryl urea)$_{1-100}$, ($C_{10-80}$ alkylaryl urea)$_{1-100}$, ($C_{10-80}$ arylalkyl urea)$_{1-100}$, ($C_{2-50}$ alkyl amide)$_{1-100}$, ($C_{7-60}$ aryl amide)$_{1-100}$, ($C_{8-70}$ alkylaryl amide)$_{1-100}$, ($C_{8-70}$ arylalkyl amide)$_{1-100}$, ($C_{3-30}$ alkyl anhydride)$_{1-100}$, ($C_{8-50}$ aryl anhydride)$_{1-100}$, ($C_{9-60}$ alkylaryl anhydride)$_{1-100}$, ($C_{9-60}$ arylalkyl anhydride)$_{1-100}$, ($C_{2-30}$ alkyl carbonate)$_{1-100}$, ($C_{7-50}$ aryl carbonate)$_{1-100}$, ($C_{8-60}$ alkylaryl carbonate)$_{1-100}$, ($C_{8-60}$ arylalkyl carbonate)$_{1-100}$, —$R_1$—O—CO—NH—($R_2$ or Ar—$R_2$—Ar)—NH—CO—O—($C_{1-30}$ alkyl ether, $C_{6-40}$ aryl ether, $C_{7-60}$ alkylaryl ether, or $C_{7-60}$ arylalkyl ether)$_{1-100}$, —$R_1$—O—CO—NH—($R_2$ or Ar—$R_2$—Ar)—NH—CO—O—($C_{2-50}$ alkyl ester, $C_{7-60}$ aryl ester, $C_{8-70}$ alkylaryl ester, or $C_{8-70}$ arylalkyl ester)$_{1-100}$, —$R_1$—O—CO—NH—($R_2$ or Ar—$R_2$—Ar)—NH—CO—O—($C_{1-30}$ alkyl ether, $C_{6-40}$ aryl ether, $C_{7-60}$ alkylaryl ether, or $C_{7-60}$ arylalkyl ether)$_{1-100}$—CO—NH—($R_2$ or Ar—$R_2$—Ar)—NH—CO—O—, —$R_1$—O—CO—NH—($R_2$ or Ar—$R_2$—Ar)—NH—CO—O—($C_{2-50}$ alkyl ester, $C_{7-60}$ aryl ester, $C_{8-70}$ alkylaryl ester, or $C_{8-70}$ arylalkyl ester)$_{1-100}$—$R_3$—O—CO—NH—($R_2$ or Ar—$R_2$—Ar)—NH—CO—O—, —$R_1$—NH—CO—NH—($R_2$ or Ar—$R_2$—Ar)—NH—CO—O—($C_{1-30}$ alkyl ether, $C_{6-40}$ aryl ether, $C_{7-60}$ alkylaryl ether, or $C_{7-60}$ arylalkyl ether)$_{1-100}$, —$R_1$—NH—CO—NH—($R_2$ or Ar—$R_2$—Ar)—NH—CO—O—($C_{2-50}$ alkyl ester, $C_{7-60}$ aryl ester, $C_{8-70}$ alkylaryl ester, or $C_{8-70}$ arylalkyl ester)$_{1-100}$, —$R_1$—NH—CO—NH—($R_2$ or Ar—$R_2$—Ar)—NH—CO—O—($C_{1-30}$ alkyl ether, $C_{6-40}$ aryl ether, $C_{7-60}$ alkylaryl ether, or $C_{7-60}$ arylalkyl ether)$_{1-100}$—CO—NH—($R_2$ or Ar—$R_2$—Ar)—NH—CO—O—, —$R_1$—NH—CO—NH—($R_2$ or Ar—$R_2$—Ar)—NH—CO—O—($C_{2-50}$ alkyl ester, $C_{7-60}$ aryl ester, $C_{8-70}$ alkylaryl ester, or $C_{8-70}$ arylalkyl ester)$_{1-100}$—$R_3$—O—CO—NH—($R_2$ or Ar—$R_2$—Ar)—NH—CO—O—, —$R_1$—O—CO—NH—($R_2$ or Ar—$R_2$—Ar)—NH—CO—NH—($C_{2-50}$ alkyl amide, $C_{7-60}$ aryl amide, $C_{8-70}$ alkylaryl amide, or $C_{8-70}$ arylalkyl amide)$_{1-100}$, or —$R_1$—NH—CO—NH—($R_2$ or Ar—$R_2$—Ar)—NH—CO—NH—($C_{2-50}$ alkyl amide, $C_{7-60}$ aryl amide, $C_{8-70}$ alkylaryl amide, or $C_{8-70}$ arylalkyl amide)$_{1-100}$;

each Z is —C—D, wherein C is independently —R—, —R—Ar—, —Ar—, or —Ar—R—; and D is independently —OH, —SH, —$SO_3^-$, —$OSO_3^-$, —$CO_2^-$, —$PO_3^-$, —O—$PO_3^{-2}$, —O—PO(O$^-$)—O—$PO_3^{-2}$, —O—PO(O$^-$)—O—PO(O$^-$)O—$PO_3^{-2}$, —O—PO(O$^-$)—O—$CH_2$—$CH_2$—$NH_3^+$, —$NH_2$, —$NH_3^+$, —$N^+H_2R_b$, —$N^+HR_bR_c$, or —$N^+R_bR_cR_d$; and m is 0–30 (e.g., 0, or 0–16), n is 0–30 (e.g., 0–16, 4–16, or 2–30), and the sum of m and n is 2–30 (e.g., 4–16);

in which each of R, $R_1$, $R_2$, $R_3$, $R_a$, $R_b$, $R_c$, and $R_d$ is independently $C_{1-20}$ alkyl, and Ar is independently $C_{6-40}$ aryl (e.g., p-phenylene abbreviated as Ph herein).

Another aspect of this invention features a group of compounds of the following formula and their counter ionic salts:

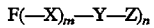

wherein

F is a fullerene core;

each X is independently —$CO_2^-$, —$SO_3^-$, —OH, —SH, —$PO_3^-$, —O—$PO_3^{-2}$, —O—PO(O$^-$)—O—$PO_3^{-2}$, —O—PO(O$^-$)—O—PO(O$^-$)—O—$PO_3^{-2}$, —O—PO(O$^-$)—O—$CH_2$—$CH_2$—$NH_3^+$, —$NH_2$, —$NH_3^+$, —$N^+H_2R_a$, —$N^+HR_aR_b$, or —$N^+R_aR_bR_c$;

each Y is —A—B—, in which A is independently —$CH_2$—, —O—, —S—, —NH—CO—NH—, or —NH—CO—; and B is independently —$R_d$—O—[Si(CH$_3$)$_2$—O—]$_{1-100}$, $C_{1-2000}$ alkyl (a divalent radical), $C_{6-40}$ aryl (a divalent radical), $C_{7-60}$ alkylaryl (a divalent radical), $C_{7-60}$ arylalkyl (a divalent radical), ($C_{1-30}$ alkyl ether)$_{1-100}$, ($C_{6-40}$ aryl ether)$_{1-100}$, ($C_{7-60}$ alkylaryl ether)$_{1-100}$, ($C_{7-60}$ arylalkyl ether)$_{1-100}$, ($C_{1-30}$ alkyl thioether)$_{1-100}$, ($C_{6-40}$ aryl thioether)$_{1-100}$, ($C_{7-60}$ alkylaryl thioether)$_{1-100}$, ($C_{7-60}$ arylalkyl thioether)$_{1-100}$, ($C_{2-50}$ alkyl ester)$_{1-100}$, ($C_{7-60}$ aryl ester)$_{1-100}$, ($C_{8-70}$ alkylaryl ester)$_{1-100}$, ($C_{8-70}$ arylalkyl ester)$_{1-100}$, —R—CO—O—($C_{1-30}$ alkyl ether)$_{1-100}$, —R—CO—O—($C_{6-40}$ aryl ether)$_{1-100}$, —R—CO—O—($C_{7-60}$ alkylaryl ether)$_{1-100}$, —R—CO—O—($C_{7-60}$ arylalkyl ether)$_{1-100}$, ($C_{4-50}$ alkyl urethane)$_{1-100}$, ($C_{1-60}$ aryl urethane)$_{1-100}$, ($C_{10-80}$ alkylaryl urethane)$_{1-100}$, ($C_{10-80}$ arylalkyl urethane)$_{1-100}$, (C$_{5-50}$ alkyl urea)$_{1-100}$, (C$_{14-60}$ aryl urea)$_{1-100}$, (C$_{10-80}$ alkylaryl urea)1-100, (C$_{10-80}$ arylalkyl urea)$_{1-100}$, (C$_{2-50}$ alkyl amide)$_{1-100}$, (C$_{7-60}$ aryl amide)$_{1-100}$, (C$_{8-70}$ alkylaryl amide)$_{1-100}$, (C$_{8-70}$ arylalkyl amide)$_{1-100}$, (C$_{3-30}$ alkyl anhydride)$_{1-100}$, (C$_{8-50}$ aryl anhydride)$_{1-100}$, (C$_{9-60}$ alkylaryl anhydride)$_{1-100}$, (C$_{9-60}$ arylalkyl anhydride)$_{1-100}$, (C$_{2-30}$ alkyl carbonate)$_{1-100}$, (C$_{7-50}$ aryl carbonate)$_{1-100}$, (C$_{8-60}$ alkylaryl carbonate)$_{1-100}$, (C$_{8-60}$ arylalkyl carbonate)$_{1-100}$, —R$_1$—O—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$, —R$_1$—O—CO—NH—(R$_2$ or Ar—R$_2$—Ar)—NH—CO—O—(C$_{2-50}$ alkyl ester, C$_{7-60}$ aryl ester, C$_{8-70}$ alkylaryl ester, or C$_{8-70}$ arylalkyl ester)$_{1-100}$, —R$_1$—O—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$—CO—NH—(R$_2$ or Ar—R$_2$—Ar)—NH—CO—O—, —R$_1$—O—CO—NH—(R$_2$ or Ar—R$_2$—Ar)—NH—CO—O—(C$_{2-50}$ alkyl ester, C$_{7-60}$ aryl ester, C$_{8-70}$ alkylaryl ester, or C$_{8-70}$ arylalkyl ester)$_{1-100}$—R$_3$—O—CO—NH—(R$_2$ or Ar—R$_2$—Ar)—NH—CO—O—, —R$_1$—NH—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$, —R$_1$—NH—CO—NH—(R$_2$ or Ar—R$_2$—Ar)—NH—CO—O—(C$_{2-50}$ alkyl ester, C$_{7-60}$ aryl ester, C$_{8-70}$ alkylaryl ester, or C$_{8-70}$ arylalkyl ester)$_{1-100}$, —R$_1$—NH—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$—CO—NH—(R$_2$ or Ar—R$_2$—Ar)—NH—CO—O—, —R$_1$—NH—CO—NH—(R$_2$ or Ar—R$_2$—Ar)—NH—CO—O—(C$_{2-50}$ alkyl ester, C$_{7-60}$ aryl ester, C$_{8-70}$ alkylaryl ester, or C$_{8-70}$ arylalkyl ester)$_{1-100}$—R$_3$—O—CO—NH—(R$_2$ or Ar—R$_2$—Ar)—NH—CO—O—, —R$_1$—O—CO—NH—(R$_2$ or Ar—R$_2$—Ar)—NH—CO—NH—(C$_{2-50}$ alkyl amide, C$_{7-60}$ aryl amide, C$_{8-70}$ alkylaryl amide, or C$_{8-70}$ arylalkyl amide)$_{1-100}$, or —R$_1$—NH—CO—NH—(R$_2$ or Ar—R$_2$—Ar)—NH—CO—NH—(C$_{2-50}$ alkyl amide, C$_{7-60}$ aryl amide, C$_{8-70}$ alkylaryl amide, or C$_{8-70}$ arylalkyl amide)$_{1-100}$;

each Z is —C—D, wherein C is independently —R—, —R—Ar—, —Ar—, or —Ar—R—; and D is independently —OH, —SH, —SO$_3^-$, —OSO$_3^-$, —CO$_2^-$, —PO$_3^-$, —O—PO$_3^{-2}$, —O—PO)O$^-$)—O—PO$_3^{-2}$, —O—PO (O$^-$) —O—PO (O$^-$)O—PO$_3^{-2}$, —O—PO(O$^-$)—O—CH$_2$—CH$_2$—NH$_3^+$, —NH$_2$, —NH$_3^+$, —N$^+$H$_2$R$_{a'}$, —N$^+$HR$_a$R$_{b'}$, or —N$^+$R$_a$R$_b$R$_c$; and m is 0–30 (e.g., 0 or 0–16), n is 1–30 (e.g., 1–16 or 2–30), and the sum of m and n is 2–30 (e.g., 4–16);

in which each of R, R$_1$, R$_2$, R$_3$, R$_a$, R$_b$, R$_c$, R$_d$, R$_{a'}$, R$_{b'}$, and R$_c$, is independently C$_{1-20}$ alkyl, and Ar is independently C$_{6-40}$ aryl.

Also within the scope of this invention is a composition including a biologically compatible substance and a compound of the following formula and their counter ionic salts:

F(—X)$_m$(—Y—Z)$_n$ wherein

F is a fullerene core;

each X is independently —CO$_2^-$, —SO$_3^-$, —SH, —OH, —PO$_3^-$, —O—PO$_3^{-2}$, —O—PO(O$^-$)—O—PO$_3^{-2}$, —O—PO(O$^-$)—O—PO(O$^-$)—O—PO$_3^{-2}$, —O—PO(O$^-$) —O—CH$_2$—CH$_2$—NH$_3^+$, —NH$_2$, —NH$_3^+$, —N$^+$H$_2$R$_{a'}$, —N$^+$HR$_a$R$_b$, or —N$^+$R$_a$R$_b$R$_c$;

each Y is —A—B—, in which A is independently —CH$_2$—, —O—, —NH—, —S—, —O—CO—, —O—CO—O—, —O—CO—NH—, —NH—CO—NH—, or —NH—CO—; and B is independently —R$_d$—O—[Si (CH$_3$)$_2$—O—]$_{1-100}$, C$_{1-2000}$ alkyl (a divalent radical), C$_{6-40}$ aryl (a divalent radical), C$_{7-60}$ alkylaryl (a divalent radical), C$_{7-60}$ arylalkyl (a divalent radical), (C$_{1-30}$ alkyl ether)$_{1-100}$, (C$_{6-40}$ aryl ether)$_{1-100}$, (C$_{7-60}$ alkylaryl ether)$_{1-100}$, (C$_{7-60}$ arylalkyl ether)$_{1-100}$, (C$_{1-30}$ alkyl thioether)$_{1-100}$, (C$_{6-40}$ aryl thioether)$_{1-100}$, (C$_{7-60}$ alkylaryl thioether)$_{1-100}$, (C$_{7-60}$ arylalkyl thioether)$_{1-100}$, (C$_{2-50}$ alkyl ester)$_{1-100}$, (C$_{7-60}$ aryl ester)$_{1-100}$, (C$_{8-70}$ alkylaryl ester)$_{1-100}$, (C$_{8-70}$ arylalkyl ester)$_{1-100}$, —R—CO—O—(C$_{1-30}$ alkyl ether)$_{1-100}$, —R—CO—O—(C$_{6-40}$ aryl ether)$_{1-100}$, —R—CO—O—(C$_{7-60}$ alkylaryl ether)$_{1-100}$, —R—CO—O—(C$_{7-60}$ arylalkyl ether)$_{1-100}$, (C$_{4-50}$ alkyl urethane)$_{1-100}$, (C$_{14-60}$ aryl urethane)$_{1-100}$, (C$_{10-80}$ alkylaryl urethane)$_{1-100}$, (C$_{10-80}$ arylalkyl urethane)$_{1-100}$, (C$_{5-50}$ alkyl urea)$_{1-100}$, (C$_{14-60}$ aryl urea)$_{1-100}$, (C$_{10-80}$ alkylaryl urea)$_{1-100}$, (C$_{10-80}$ arylalkyl urea)$_{1-100}$, (C$_{2-50}$ alkyl amide)$_{1-100}$, (C$_{7-60}$ aryl amide)$_{1-100}$, (C$_{8-70}$ alkylaryl amide)$_{1-100}$, (C$_{8-70}$ arylalkyl amide)$_{1-100}$, (C$_{3-30}$ alkyl anhydride)$_{1-100}$, (C$_{8-50}$ aryl anhydride)$_{1-100}$, (C$_{9-60}$ alkylaryl anhydride)$_{1-100}$, (C$_{9-60}$ arylalkyl anhydride)$_{1-100}$, (C$_{2-30}$ alkyl carbonate)$_{1-100}$, (C$_{7-50}$ aryl carbonate)1-100, (C$_{8-60}$ alkylaryl carbonate)$_{1-100}$, (C$_{8-60}$ arylalkyl carbonate)$_{1-100}$, —R$_1$—O—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$, —R$_1$—O—CO—NH—(R$_2$ or Ar—R$_2$—Ar)—NH—CO—O—(C$_{2-50}$ alkyl ester, C$_{7-60}$ aryl ester, C$_{8-70}$ alkylaryl ester, or C$_{8-70}$ arylalkyl ester)$_{1-100}$, —R$_1$—O—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$—CO—NH—(R$_2$ or Ar—R$_2$—Ar)—NH—CO—O—, —R$_1$—O—CO—NH—(R$_2$ or Ar—R$_2$—Ar)—NH—CO—O—(C$_{2-50}$ alkyl ester, C$_{7-60}$ aryl ester, C$_{8-70}$ alkylaryl ester, or C$_{8-70}$ arylalkyl ester)$_{1-100}$—R$_3$—O—CO—NH—(R$_2$ or Ar—R$_2$—Ar)—NH—CO—O—, —R$_1$—NH—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$, —R$_1$—NH—CO—NH—(R$_2$ or Ar—R$_2$—Ar)—NH—CO—O—(C$_{2-50}$ alkyl ester, C$_{7-60}$ aryl ester, C$_{8-70}$ alkylaryl ester, or C$_{8-70}$ arylalkyl ester)$_{1-100}$, —R$_1$—NH—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$—CO—NH—(R$_2$ or Ar—R$_2$—Ar)—NH—CO—O—, —R$_1$—NH—CO—NH—(R$_2$ or Ar—R$_2$—Ar)—NH—CO—O—(C$_{2-50}$ alkyl ester, C$_{7-60}$ aryl ester, C$_{8-70}$ alkylaryl ester, or C$_{8-70}$ arylalkyl ester)$_{1-100}$—R$_3$—O—CO—NH—(R$_2$ or Ar—R$_2$—Ar)—NH—CO—O—, —R$_1$—O—CO—NH—(R$_2$ or Ar—R$_2$—Ar)—NH—CO—NH—(C$_{2-50}$ alkyl amide, C$_{7-60}$ aryl amide, C$_{8-70}$ alkylaryl amide or C$_{8-70}$ arylalkyl amide)$_{1-100}$, or —R$_1$—NH—CO—NH—(R$_2$ or Ar—R$_2$—Ar)—NH—CO—NH—(C$_{2-50}$ alkyl amide, C$_{7-60}$ aryl amide, C$_{8-70}$ alkylaryl amide, or C$_{8-70}$ arylalkyl amide)$_{1-100}$;

each Z is —C—D, wherein C is independently —R—, —R—Ar—, —Ar—, or —Ar—R—; and D is independently —H, —OH, —SH, —SO$_3^-$, —OSO$_3^-$, —CO$_2^-$, —PO$_3^-$, —O—PO$_3^{-2}$, —O—PO(O$^-$)—O—PO$_3^{-2}$, —O—PO(O$^-$)—O—PO(O$^-$)O—PO$_3^{-2}$, —O—PO(O$^-$)—O—CH$_2$—CH$_2$—NH$_3^+$, —NH$_2$, —NH$_2^+$, —N$^+$H$_2$R$_{a'}$, —N$^+$HR$_a$R$_{b'}$, or —N$^+$R$_a$R$_b$R$_c$; and m is 0–30 (e.g., 1–16, or 1–12), n is 0–30 (e.g., 0–16, or 0–12), and the sum of m and n is 2–30 (e.g., 4–16, or 6–12);

in which each of R, R$_1$, R$_2$, R$_3$, R$_a$, R$_b$, R$_c$, R$_d$, R$_{a'}$, R$_{b'}$, and R$_c$, is independently C$_{1-20}$ alkyl, and Ar is independently C$_{6-40}$ aryl.

What is meant by "a biologically compatible substance" is a substance other than water which has no toxicity and is intended to be ingested by or otherwise brought into contact with human bodies, e.g., a substance that is contained in a pharmaceutical (drug or vitamin) product, a cosmetic product, a skin-care product, a food product, or a cigarette. Examples of compositions of this invention include, but are not limited to, a pharmaceutical forumulation containing a free-radical scavenging fullerene derivative and an excipient, and a cigarette filter with a free-radical scavenging fullerene derivative covalently or non-covalently dispersed in it.

What is meant by "fullerene core" is a caged molecule consisting essentially of carbon atoms such as $C_{60}$, $C_{60}H_x$, $C_{61}$, $C_{62}$, $C_{71}$, $C_{72}$, $C_{60}O_x$, $C_{60}N_x$, $C_{61}O_x$, $C_{62}O_x$, $C_{70}O_x$, $C_{71}O_x$, $C_{72}O_x$, $C_{70}N_x$, $C_{76}$, $C76O_x$, $C_{78}$, $C_{78}O_x$, $C_{82}$, $C82O_x$, $C_{84}$, $C_{84}O_x$, $C_{92}$, $C_{92}O_x$, and the like, in which x is 1–20 (e.g., 1–8). $C_{60}O_x(OH)_y$ is an example of a fullerene derivative in which $C_{60}O_x$ is the fullerene core with hydroxyl groups linked to it. $C_{60}H_x(NRR')_x$, on the other hand, is an example where $C_{60}H_x$ is the fullerene cage.

The structures of many of the moieties mentioned above are shown below within the pair of parentheses following each of the moieties: alkyl ether (—R—O—), aryl ether (—Ar—O—), alkylaryl ether (—R—Ar—O—), arylalkyl ether (—Ar—R—O—), alkyl thioether (—R—S—), aryl thioether (—Ar—S—), alkylaryl thioether (—R—Ar—S—), arylalkyl thioether (—Ar—R—S—), alkyl ester (—R—O—CO—, —R—CO—O—, —R$_1$—CO—O—R$_2$—O—CO—, or—R$_1$—O—CO—R$_2$—CO—O—), aryl ester (—Ar—O—CO—, —Ar—CO—O—, —Ar$_1$—CO—O—Ar$_2$—O—CO—, or —Ar$_1$—O—CO—Ar$_2$—CO—O—), alkylaryl ester (—R—Ar—O—CO— or —R—Ar—CO—O—), arylalkyl ester (—Ar—R—O—CO— or —Ar—R—CO—O—), alkyl urethane (—R$_1$—O—CO—NH—R$_2$—NH—CO—O—), aryl urethane (—Ar$_1$—O—CO—NH—Ar$_2$—NH—CO—O—), alkylaryl urethane (—R$_1$—Ar—O—CO—NH—R$_2$—NH—CO—O—, —R—Ar$_1$—O—CO—NH—Ar$_2$—NH—CO—O—, or —R$_1$—O—CO—NH—Ar—R$_2$—Ar—NH—CO—O—), arylalkyl urethane (—Ar—R$_1$—O—CO—NH—R$_2$—NH—CO—O—, —Ar$_1$—R—O—CO—NH—Ar$_2$—NH—CO—O—, or —Ar$_1$—O—CO—NH—Ar$_2$—R—Ar$_2$—NH—CO—O—), alkyl urea (—R$_1$—NH—CO—NH—R$_2$—NH—CO—NH—), aryl urea (—Ar$_1$—NH—CO—NH—Ar$_2$—NH—CO—NH—), alkylaryl urea (—R$_1$—Ar—NH—CO—NH—R$_2$—NH—CO—NH—, —R—Ar$_1$—NH—CO—NH—Ar$_2$—NH—CO—NH—, or —R$_1$—NH—CO—NH—Ar—R$_2$—Ar—NH—CO—NH—), arylalkyl urea (—Ar—R$_1$—NH—CO—NH—R$_2$—NH—CO—NH—, —Ar$_1$—R—NH—CO—NH—Ar$_2$—NH—CO—NH—, or —Ar$_1$—NH—CO—NH—Ar$_2$—R—Ar$_2$—NH—CO—NH—), alkyl amide (—R—NH—CO—, —R—CO—NH—, —R$_1$—CO—NH—R$_2$—NH—CO—, or —R$_1$—NH—CO—R$_2$—CO—NH—), aryl amide (—Ar—NH—CO—, —Ar—CO—NH—, —Ar$_1$—CO—NH—Ar$_2$—NH—CO—, or —Ar$_1$—NH—CO—Ar$_2$—CO—NH—), alkylaryl amide (—R—Ar—NH—CO—, —R—CO—NH—Ar—NH—CO—, or —R—NH—CO—Ar—CO—NH—), arylalkyl amide (—Ar—R—NH—CO—, —Ar—CO—NH—R—NH—CO—, or —Ar—NH—CO—R—CO—NH—), alkyl anhydride (—R—CO—O—CO—), aryl anhydride (—Ar—CO—O—CO—), alkylaryl anhydride (—R—Ar—CO—O—CO— or —R—CO—O—CO—Ar—CO—O—CO—), arylalkyl anhydride (—Ar—R—CO—O—CO— or —Ar—CO—O—CO—R—CO—O—CO—), alkyl carbonate (—R—O—CO—O—), aryl carbonate (—Ar—O—CO—O—), alkylaryl carbonate (—R—Ar—O—CO—O— or —R—O—CO—O—Ar—O—CO—O—), and arylalkyl carbonate (—Ar—R—O—CO—O— or —Ar—O—CO—O—R—O—CO—O—). Note that the symbols R, R$_1$, R$_2$, and Ar used in this paragraph do not necessarily have the same carbon numbers as the same symbols used elsewhere in this disclosure.

One can use fullerene derivatives described herein to detect free radicals in the blood of a patient in a manner identical or analogous to that shown in Example 18 below. Alternatively, such fullerene derivatives can be used as free-radical scavenging agents in a cigarette filter or in a device attached to a cigarette for absorbing gas phase reactive free radicals, especially $NO_x$ radicals such as .NO and $.NO_2$ generated from the combustion of tobacco leaves. They can also be used as antioxidant additives in food products, as substitutes for vitamin C, as anti-aging agents in skin-care lotions and cosmetic products. Clinic applications include: reducing free radicals in ischemia reperfusion injuries; inhibiting tissue and cell damages induced by acute pancreatitis, various cancers (e.g., gastric cancer, breast cancer, or ovarian cancer), and other free-radical related diseases such as diabetes and neurodegenerative diseases (e.g., Alzheimer's disease, Parkinson's disease, and amyotrophic lateral sclerosis); suppressing proliferation of cancer cells and smooth muscle cells (e.g., as in atherosclerosis and restenosis). Indeed, more and more injuries and diseases have been found to be linked to free radical-mediated disturbances.

Thus, within the scope of this invention are (1) a pharmaceutical composition containing any of the fullerene derivatives described herein for use as a free radical-scavenging agent to treat a disorder or diseases associated with high levels of free radicals; and (2) the use of a pharmaceutical composition containing a free radical-scavenging agent (as described herein) for the manufacture of a medicament for the treatment of such disorders or diseases.

The dose of a pharmaceutical composition of this invention varies depending upon the manner of administration, the age and the body weight of the subject and the condition of the subject to be treated, and ultimately will be decided by the attending physician or veterinarian. The formulations may conveniently be presented in unit dosage form and may be prepared by any of the methods well known in the art of pharmacy. All methods include the step of bringing the active ingredient(s) into association with the carrier which constitutes one or more accessory ingredients. In general, the formulations for tablets or powders are prepared by uniformly and intimately blending the active ingredient with finely divided solid carriers, and then, if necessary as in the case of tablets, forming the product into the desired shape and size.

Other features or advantages of the present invention will be apparent from the following drawings and detailed description of several embodiments, and also from the appending claims.

BRIEF DESCRIPTION OF THE DRAWINGS

The drawings are first described.

DETAILED DESCRIPTION OF THE INVENTION

Figure 1:
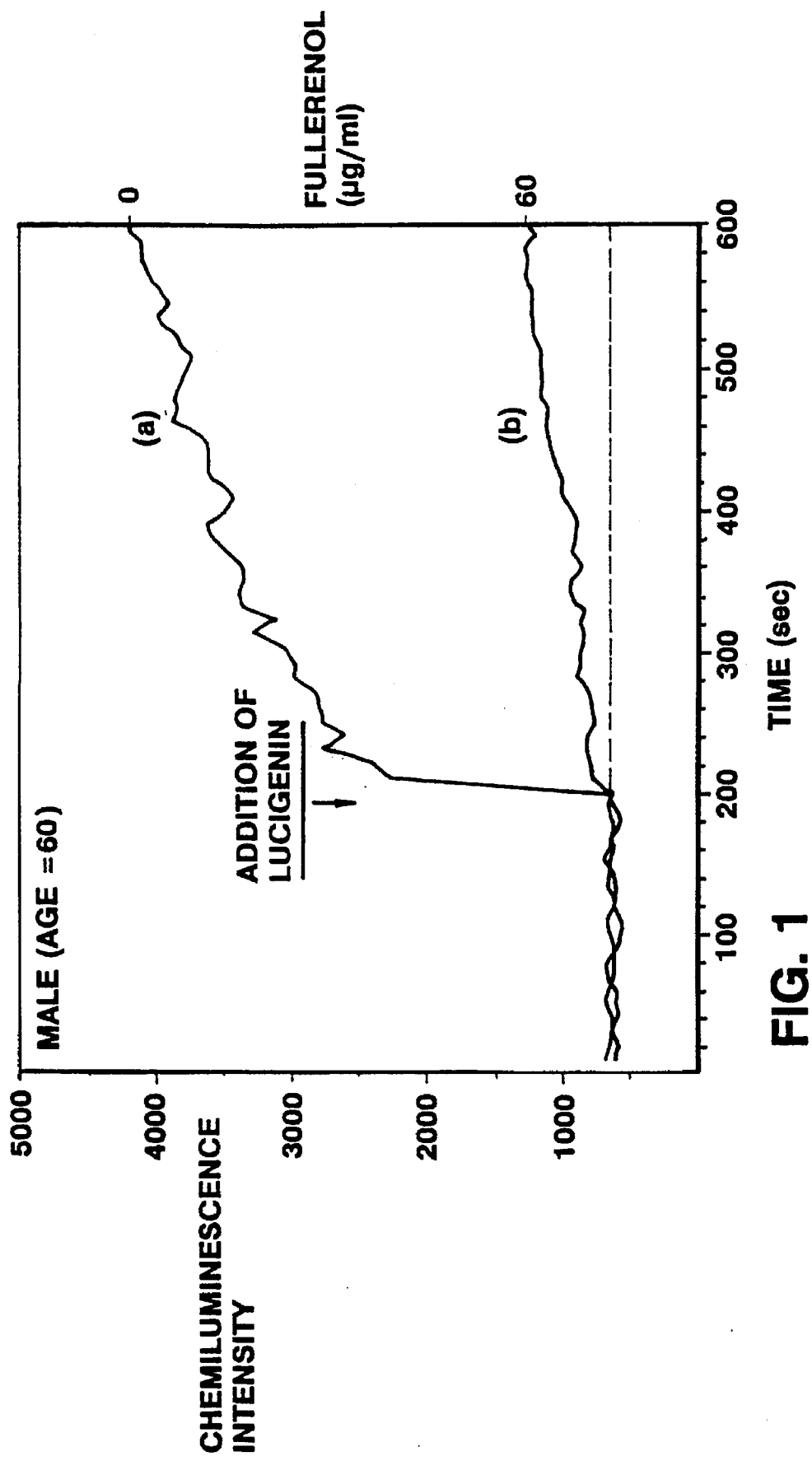
FIG. 1 is a graph showing chemiluminescence intensity levels of whole blood from a male patient with acute pancreatitis: (a) no pretreatment with a fullerenol; and (b) pretreatment with a fullerenol.

Described below are various methods for synthesizing some of the free-radical scavenging fullerene derivatives described herein.

Water-soluble polyhydroxylated fullerene derivatives, $C_{60}(OH)_x$, or polyoxy-hydroxylated fullerene derivatives, $C_{60}O_x(OH)_y$, can be prepared by one of the following six methods:

(a) Fullerenol-1 can be prepared from hydrolysis of the reaction products of fullerenes, either pure $C_{60}$ or a mixture of $C_{60}$ (84%) and $C_{70}$ (16%), with nitronium tetrafluoroborate in the presence of organocarboxylic acid ($RCO_2H$) at ambient temperature. Chiang, et al., U.S. Pat. Nos. 5,177, 248; et al. 5,294,732; and et al., J. Am. Chem. Soc. 1992, 114, 10154; Chiang, et al., J. Am. Chem. Soc. 1993, 115, 5453. The structure of fullerenol-1 has been characterized to consist of $C_{60}O_x(OH)_y$ with x<5 and y=18 on average.

(b) Fullerenol-2 can be synthesized via hydrolysis of the reaction products of fullerenes, either pure $C_{60}$ or a mixture of $C_{60}$ (85%) and $C_{70}$ (16%), with a solution of sulfur trioxide (30%) in sulfuric acid. See Chiang, et al., J. Org. Chem. 1994, 59, 3960. The structure of fullerenol-2 has been characterized to consist of $C_{60}(OH)_y$ with y=12 on average.

(c) Fullerenol-3 can be prepared by the reaction of fullerenes with either a mixture of conc. $H_2SO_4$, conc. $HNO_3$ and water at 90° C. or a mixture of oleum ($H_2SO_4$—$SO_3$), $KNO_2$ and water. See Chiang, et al., U.S. Pat. Nos. 5,177,248; 5,294,732; J. Chem. Soc., Chem. Commun. 1992, 1791; Chiang, et al., Mat. Res. Soc. Symp. Proc. 1992, 247. The structure of fullerenol-3 has been characterized to consist of $C_{60}O_x(OH)_y$ with x<5 and y=15 on average.

(d) Fullerenol-4 can be synthesized by the reaction of fullerenes, dissolved in either benzene or toluene, with aqueous sodium hydroxide in the presence of a catalytic amount of tetrabutylammonium hydroxide and oxygen (in air). See Li, et al., J. Chem. Soc., Chem. Commun. 1993, 1784. The structure of fullerenol-4 has been characterized to consist of polyhydroxylated $C_{60}$ fullerene derivatives with 26 hydroxy groups per $C_{60}$ cage on average.

(e) Fullerenol-5 can be prepared by the reaction of fullerenes, dissolved in either benzene or toluene, and gaseous nitrogen dioxide, followed by hydrolysis of resulting products with aqueous NaOH. See Chiang, et al., Tetrahedron, "Efficient Onw-Flask Synthesis of Water-soluble [60]Fullerenols," in press. Gaseous nitrogen dioxide can be generated by either reacting $NaNO_2$ with $FeSO_4$ in aqueous $H_2SO_4$ in the presence of air (Roy, et al., J. Chem. Soc., Chem. Commun. 1994, 275) or reacting $NaNO_2$ with conc. $HNO_3$. The former method yield nitrofullerenols consisting 6–8 nitro and 7–12 hydroxy groups per $C_{60}$. Hydrolysis of these products results in fullerenols with 13–20 hydroxy groups per $C_{60}$. The later method gives water-soluble fullerenols with a maximum number of hydroxy groups per $C_{60}$ as 20 as identified by the FAB mass spectroscopy.

(f) Fullerenol-6 can be synthesized by the reaction of fullerenes with an excess of $BH_3$-tetrahydrofuran (THF) complex followed by hydrolysis with either sodium hydroxide/hydrogen peroxide or sodium hydroxide. See Schneider, et al., J. Chem. Soc., Chem. Commun. 1994, 463.

Polyaminohydroxylated fullerene derivatives, $C_{60}(OH)_x(NH_2)_y$, or polyoxyaminohydroxylated fullerene derivatives, $C_{60}O_x(OH)_y(NH_2)_z$, can be prepared from hydrolysis of the reaction products of fullerenes, either pure $C_{60}$ or a mixture of $C_{60}$ (84%) and $C_{70}$ (16%), with nitronium tetrafluoroborate in the presence of organocarbamide ($RCONH_2$) at ambient temperature. See Chiang et al., U.S. Pat. Nos. 5,177,248; and 5,294,732.

Dialkyl or diaryl methano-bridged fullerene derivatives, $C_{61}(R)_2$ or $C_{61}(—C_6H_5—R)_2$, can be synthesized by one the three following methods:

(a) Dialkyl or diaryl methano-bridged fullerene derivatives $C_{61}(R)_2$ or $C_{61}(—C_6H_5—R)_2$ can be prepared from the reaction of $C_{60}$ fullerene with diazoalkanes or diphenyldiazomethane derivatives to give mono-addition of functionalized or non-functionalized diphenylmethane on $C_{60}$. See Suzuki, et al., Science 1991, 254, 1186; and Isaacs, et al., Helv. Chim. Acta 1993, 76, 1231.

(b) Dialkyl methano-bridged fullerene derivatives $C_{61}(R)_2$ can be prepared from the reaction of $C_{60}$ fullerene with bromomalonic acid diethyl ester and sodium hydride to give mono-addition of malonic acid diethyl ester on $C_{60}$. See Paulus, et al., Acta Cryst. 1995, C51, 143.

(c) Alkyl methano-bridged fullerene derivatives $C_{61}(R)$ can be prepared from the reaction of $C_{60}$ fullerene with 1-(4-methoxyphenyl)-1-(trimethylsilyloxy)ethylene to give the corresponding product of $C_{61}(COC_6H_4OMe)$. See Shu, et al., J. Chem. Soc., Chem. Commun. 1995, 367.

Polyalkyl fullerene derivatives, $C_{60}(R)_x$, can be synthesized by one of the two following methods:

(a) Polyalkyl fullerene derivatives can be synthesized by the reaction of fullerenes with organic alkyl radicals (R.) to give products of $C_{60}(R)_x$ with x=1 to at least 15. See Krusic, et al., Science 1991, 254, 1183.

(b) Polyalkyl fullerene derivatives can be synthesized by the reaction of fullerenes with organic alkyl lithium or alkyl Grignard reagents (R⁻) followed by reacting the resulting intermediates with alkyl halides to give products of $C_{60}(R)_x$ with x=1 to 30. See Wudl, et al., ACS Symp. Ser. 1992, 481, 161.

Polyalkylamino fullerene derivatives, $C_{60}H_x(NRR')_x$, can be synthesized by the reaction of fullerenes with alkyl amine at ambient temperature for 2 days to give the corresponding products of $C_{60}H_x(NRR')_x$ with x=6 predominately. See Hirsch, et al, Angew. Chem. Int. Ed. Engl. 1991, 30, 1309.

Monocycloalkyl, monocycloaryl, polycycloalkyl, or polycycloaryl fullerene derivatives, $C_{60}$(cyclo-R) or $C_{60}$(cyclo-Ar) where x is 1–7, can be synthesized by one of the following four methods:

(a) Monocycloaryl and polycycloaryl fullerene derivatives can be prepared by the reaction of fullerenes with benzyne to give products of $C_{60}(C_6H_4)_x$ with x=1–4. See Hoke, et al., J. Org. Chem. 1992, 57, 5069; and Tsuda, et al., Chem. Lett. 1992, 2333.

(b) Monocycloalkyl and polycycloalkyl fullerene derivatives can be synthesized by the reaction of fullerenes with enones via [2+2] photocycloaddition to give the corresponding fullerene products consisting with 1–7 enone adducts. See Wilson, et al., J. Am. Chem. Soc. 1993, 115, 8495.

(c) Monocycloaryl and dicycloaryl fullerene derivatives were synthesized by the reaction of fullerenes with o-quinodimethane via [2+4] cycloaddition to give products of $C_{60}(—CH_2C_6H_4CH_2—)_x$ with x=1 or 2. Belik, et al., Angew. Chem. Int. Ed. Engl. 1993, 32, 78.

(d) Monocycloalkyl fullerene derivative can be synthesized by the reaction of $C_{60}$ fullerene with 7-alkylidene-2, 3-diazabicycloheptene via [2+3] cycloaddition to give the corresponding methylene-cyclopentane mono-adduct of fullerene, $C_{60}(—cyclopentene—CH_2—)$. See Prato, et al., J. Am. Chem. Soc. 1993, 115, 1594.

The radical-scavenging fullerene derivatives which are substituted with polymeric chains can be prepared by either one-step or multiple-step synthesis involving the reaction of a functional precursor at the connecting junction of each chain. For example, the ester connecting junction (—O—CO—) is performed by reacting an organic alcohol with an organic acid chloride or with an organic acid in the presence of a catalytic amount of Lewis acid. The urethane connecting junction (—O—CO—NH—) is performed by reacting an organic alcohol with an isocyanated organic compound. The urea connecting junction (—NH—CO—NH—) is performed by reacting an organic amine with an isocyanated organic compound. The amide (—NH—CO—) connecting junction is performed by reacting an organic amine with an organic acid chloride or with an organic acid in the presence of a catalytic amount of Lewis acid. The carbonate connecting junction (—O—CO—O—) is performed by reacting organic alcohols with phosgene (Cl—CO—Cl) in the presence of triethylamine. The anhydride connecting junction (—CO—O—CO—) is performed by reacting an organic acid with an organic acid chloride in the presence of triethylamine. Other precursors such as alkyls (alkanes, functional alkanes, and functional polyolefins), ethers (functional alkyl ether, functional aryl ether, functional alkylaryl ether, and functional arylalkyl ether), thioethers (functional alkyl thioether, functional aryl thioether, functional alkylaryl thioether, and functional arylalkyl thioether), and functional poly(dialkyl silicone oxide) are available commercially.

Fullerene derivatives containing mixed substituents chemically bonded onto a common fullerene cage can be synthesized in a stepwise manner by introducing a first group of substituents according to one of the methods described in Examples 1–19, isolating the resulting fullerene derivatives, protecting certain functionalities if necessary, and then introducing a second group of substituents according to one of the other methods described in Examples 1–19. As an example, poly(sodium sulfonylbutylated) fullerenes, $C_{60}(CH_2CH_2CH_2CH_2SO_3Na)_x$, are synthesized according to the method described in Example 9. They can then be hydroxylated by one of the methods described in Examples 1, 5, and 6, as well as methods (a)–(c) set forth above to afford the corresponding mixed-functional fullerenes $C_{60}(CH_2CH_2CH_2CH_2SO_3Na)_x(OH)_y$. Further conversion of hydroxy groups to urethanic groups can be carried out by the treatment of them with isocyanated organics, OCN—B—C—D (B, C, and D being any of the moieties assigned to them respectively in the "Summary of the Invention" section) to give fullerene derivatives $C_{60}(CH_2CH_2CH_2CH_2SO_3Na)_x(O—CO—NH—B—C—D)_y$.

Examples 1–19 below provide other synthetic methods for preparing fullerene derivatives which are capable of scavenging free radicals. Examples 20–22, on the other hand, demonstrate some utilities of such fullerene-based compounds.

Without further elaboration, it is believed that one skilled in the art can, based on the description herein, utilize the present invention to its fullest extent. The following specific examples are, therefore, to be construed as merely illustrative, and not limitative of the remainder of the disclosure in any way whatsoever. All publications recited above and in the examples are hereby incorporated by reference.

EXAMPLE 1

Synthesis of Water-Soluble Polyhydroxylated Fullerene Derivatives $C_{60}(OH)_x$ (Fullerenol-7)

A reaction flask (100 ml) was charged with fullerenes (1.0 g), either pure $C_{60}$ or a mixture of $C_{60}$ and $C_{70}$, dissolved in toluene (50 ml) and an aqueous solution containing ammonium persulfate ($(NH_4)_2S_2O_8$, 2.0 g), tetrabutylammonium chloride (300 mg) or tricaprylyl-methylammonium chloride (aliquat 336, 0.6 g), dibasic sodium phosphate ($Na_2HPO_4$, 2.0 g), and distilled water (20 ml). The solution mixture was purged with $N_2$ for 10 min prior to heating at 80° C. for 4–16 h. During the period of heating, the color of solution was observed to transfer from the toluene layer to the aqueous layer progressively with partially suspended brown solids as intermediates. At the end of reaction, the resulting mixture was added methanol (60 ml) to effect precipitation of brown solids. The solid precipitate was isolated by centrifugation. It was then washed twice with a mixture of methanol and $H_2O$ (3:1, 30 ml each time) and dried in vacuum at 40° C. to afford brown solids of polyhydroxylated fullerene derivatives $C_{60}(OH)_x$ (850–950 mg, fullerenol-7). The number of hydroxy addends on the $C_{60}$ cage increased upon the increase of heating period. The solubility of fullerenol-7 in water increased with the increase of the number of hydroxy addends. In general, fullerenol with less than 12 hydroxy groups has appreciable solubility in dimethylformamide (DMF). Further purification of fullerenol-7 was carried out by the rapid filtration of fullerenol-7 in $H_2O$-DMF solution through a column packed with Dowex ion exchange resins. Infrared data of fullerenol-7 are as follows: $IRv_{max}$ (KBr) 3450 (br, OH), 1615, 1403, 1107 and 578 $cm^{-1}$.

EXAMPLE 2

Synthesis of Water-Soluble Polyhydroxylated Fullerene Derivatives $C_{60}(OH)_x$ (Fullerenol-8)

A reaction flask (100 ml) was charged with fullerenes (1.0 g), either pure $C_{60}$ or a mixture of $C_{60}$ and $C_{70}$, dissolved in toluene (50 ml) and an aqueous solution containing iron (II) sulfate ($FeSO_4$, 1.8 g), hydrogen peroxide (30% in $H_2O$, 10 ml), anionic surfactant such as sodium dodecylbenzenesulfonate (500 mg), and distilled water (20 ml). The solution mixture was purged with $N_2$ for 10 min prior to heating at 80° C. for 4–16 h. During the period of heating, the color of solution was observed to transfer from the toluene layer to the aqueous layer progressively with partially suspended brown solids as intermediates. At the end of the reaction, the resulting mixture was added methanol (60 ml) to effect precipitation of brown solids. The solid precipitate was isolated by centrifugation. It was then washed twice with a mixture of methanol and $H_2O$ (3:1, 30 ml each time) and dried in vacuum at 40° C. to afford brown solids of polyhydroxylated fullerene derivatives $C_{60}(OH)_x$ (900 mg, fullerenol-8). The number of hydroxy addends on the $C_{60}$ cage increased upon the increase of heating period. The solubility of fullerenol-8 in water increased with the increase of the number of hydroxy addends. In general, fullerenol with less than 12 hydroxy groups has appreciable solubility in DMF. Further purification of fullerenol-8 was carried out by the rapid filtration of fullerenol-8 in $H_2O$-DMF solution through a column packed with Dowex ion exchange resins. Infrared data of fullerenol-8 are as follows: $IRv_{max}$ (KBr) 3450 (br, OH), 1610, 1397, 1110 and 590 $cm^{-1}$.

EXAMPLE 3

Synthesis of Water-Compatible Polyhydroxylated Fullerene Derivatives $C_{60}(OH)_6$ or $C_{60}(OH)_8$ (Fullerenol-9)

A reaction flask (50 ml) was charged with either hexabromo-$C_{60}$ fullerene (500 mg) [see Birkett, et al., Nature 1992, 357, 479], hexachloro-$C_{60}$ fullerene (500 mg) [see Birkett, et al., J. Chem. Soc., Chem. Commun. 1993, 1230.], or octabromo-$C_{60}$ fullerene (500 mg) [see Birkett, et al., Nature 1992, 357, 479] and DMF (20 ml). The solution mixture was purged with $N_2$ for 10 min. It was then added tetramethylammonium hydroxide pentahydrate (1.1 equiv. of halogen atom in halogenated fullerene) or other tetraalkylammonium hydroxide (1.1 equiv. of halogen atom in halogenated fullerene, 40% in $H_2O$) and stirred at 70° C. for 2–5 h. At the end of reaction, the resulting solution was concentrated and added methanol (50 ml) to effect precipitation of brown solid. The solid precipitate was isolated by centrifugation. It was then washed twice with methanol (20 ml each time) and dried in vacuum at 40° C. to afford brown solid of the corresponding hexahydroxylated, $C_{60}(OH)_6$, or octahydroxylated, $C_{60}(OH)_8$, fullerene derivative (350 mg, fullerenol-9). Fullerenols of $C_{60}(OH)_6$ and $C_{60}(OH)_8$ have appreciable solubility in DMF.

EXAMPLE 4

Synthesis of Water-Soluble Polyhydroxylated Fullerene Derivatives $C_{60}(OH)_{24}$ (Fullerenol-10)

A reaction flask (50 ml) was charged tetracosabromo-$C_{60}$ fullerene (500 mg) [see Tebbe, et al., Science 1992, 256, 822] and DMF (20 ml). The solution mixture was purged with $N_2$ for 10 min. It was then added tetramethylammonium hydroxide pentahydrate (1.1 equiv. of halogen atom in tetracosabromo-$C_{60}$ fullerene) or other tetraalkylammonium hydroxide (1.1 equiv. of halogen atom in tetracosabromo-$C_{60}$ fullerene, 40% in $H_2O$) and stirred at 70° C. for 2–5 h. At the end of reaction, the resulting solution was concentrated and added methanol (50 ml) to effect precipitation of brown solids. The solid precipitate was isolated by centrifugation. It was then washed twice with methanol (20 ml each time) and dried in vacuum at 40° C. to afford brown solid of the corresponding tetracosahydroxylated, $C_{60}(OH)_{24}$, fullerene derivative (330 mg, fullerenol-10).

EXAMPLE 5

Synthesis of Water-Soluble Polyhydroxylated Fullerene Derivatives $C_{60}(OH)_x$ (Fullerenol-11)

A reaction flask (100 ml) was charged with either fullerenol-2 (1.0 g) or fullerenol-9 (1.0 g), DMF (40 ml) and hydrogen peroxide (30% in $H_2O$, 20 ml). The solution was purged with $N_2$ for 10 min prior to exposure of UV irradiation (254 nm) for 5–24 h. During the period of irradiation, the color of solution was observed to fade from brown slightly. At the end of reaction, the resulting mixture was added a mixture of tetrahydrofuran and diethyl ether in a ratio of 1:1 (60 ml) to effect a precipitation of light brown solids. The solid precipitate was isolated by centrifugation. It was then washed twice with a mixture of THF and diethyl ether in a ratio of 2:1 (30 ml each time) and dried in vacuum at 40° C. to afford brown solids of water-soluble polyhydroxylated fullerene derivatives $C_{60}(OH)_x$ (835 mg, fullerenol-11 with the number of hydroxy addends of higher than 15 per $C_{60}$ cage). The number of hydroxy addends on the $C_{60}$ cage increased upon the time increase of the sample exposure to UV irradiation. Infrared data of fullerenol-11 are as follow: IR$v_{max}$ (KBr) 3435 (br, OH), 3243 (shoulder), 1650, 1400, 1084 and 577 cm$^{-1}$.

EXAMPLE 6

Synthesis of Polyhydroxylated Fullerene Derivatives (Fullerenol-5)

A two-necked reaction flask A (50 mL) was equipped with a vertical dropping funnel with a stopcock on one neck and a connecting gas bubbling tube on the other neck. The gas-bubbling tube was attached with a drying tube ($CaCl_2$) and inserted into the second two-necked reaction flask B. The other neck of flask B was attached with a bubbling tube which was extended into a trapping flask containing aqueous sodium hydroxide solution (2N). To minimize the back-flow of moisture from alkaline solution, a drying tube ($CaCl_2$) was installed in between the flask B and the trapping flask. A steady inert gas ($N_2$) flow was allowed starting from the top of dropping funnel, through the reaction flasks A and B in sequence, into the alkaline solution in the trapping flask. The dropping funnel and the reaction flask A were charged with conc. $HNO_3$ (10 mL) and sodium nitrite ($NaNO_2$, 10 g), respectively. In the reaction flask B was placed a solution of $C_{60}$ fullerene (500 mg) in benzen (50 mL, dried over Na). The inert gas bubbling through the $C_{60}$ solution in the flask B was adjusted to a flow rate of 5 mL per min. The fullerene solution was deoxygenated for at least 5 min prior to the reaction. Conc. $HNO_3$ solution was then allowed to add dropwise into sodium nitrite solids in the flask A. Brown fume was produced immediately upon the contact of conc. $HNO_3$ with $NaNO_2$. It was carried by the steady flow of $N_2$ and bubbled through the $C_{60}$ solution in the flask B. Within 15 min of reaction, the purple solution of $C_{60}$ was changed to orange-red progressively. The mixture was stirred at ambient temperature for an additional 2 h to give a dark brown-red solution with suspended solids. At the end of reaction, excessive nitrogen dioxide ($NO_2$) was removed by $N_2$ bubbling and destroyed in the trapping solution. Benzene was then evaporated from the product solution at a reduced pressure to give dark brown solids. The solids were suspended in anhydrous n-hexane, separated from n-hexane solution by centrifugation, and dried in vacuum at 40° C. to afford brown solids of polynitro fullerene derivatives, $C_{60}(NO_2)_n$, (650 mg). IR$v_{max}$ (KBr) 1572 [s, $v_{as}$(N—O)], 1328 [s, $v_x$(N—O)], 1085, 1038, 973, 815 (6), 760, 733, 696, 545, and 466. Polynitro compound exhibits appreciable solubility in common organic solvents such as THF, DMF, $CH_2Cl_2$, $CH_3OH$, and dimethyl sulfoxide (DMSO).

Polynitro fullerene derivatives, $C_{60}(NO_2)_n$ (500 mg), were added into an aqueous solution of NaOH (3N, 25 mL). The suspension was stirred and heated at 40° C. for 4 h. It was then added slowly into MeOH (80 mL) to effect the precipitation of dark brown solids. The suspended solids were separated from solution by centrifugation, washed 3 times with methanol (15 mL each time) and dried in vacuum at 40° C. to afford brown solids of polyhydroxylated fullerene derivatives, $C_{60}(OH)_n$ (fullerenols-5, 430 mg).

One-pot synthesis of fullerenols was performed by the direct hydrolysis of polynitro fullerene derivatives without their isolation from the previous reaction with $NO_2$, as follows: At the end of fullerene nitration reaction described above (in the same reaction scale), residual nitrogen dioxide ($NO_2$) was removed by $N_2$ bubbling and destroyed in the trapping solution. Benzene was then evaporated from the product solution at a reduced pressure to give solvent-free solids. An aqueous solution of NaOH (3N, 25 mL) was added. The suspension was stirred and heated at 40° C. for 4 h. After cooling the reaction mixture to ambient temperature, it was poured slowly into MeOH (80 mL) to effect the precipitation of dark brown solids of fullerenols. The rest of the workup procedure is identical to that described above for the synthesis of fullerenol-5.

The physical data of compound $C_{60}(OH)$ n are as follow: IR$v_{max}$ (KBr) 3434 (br, s, OH), 1631, 1387, 1065, and 472; $^{13}C$ NMR (THF-$d_8$, the highest peak of band) δ 147.4, 146.0, 143.2, 72.0–84.0 (very weak). MS (FAB, negative ion, mass of the highest ion peak in the fragmentation group), m/z 576, 600, 624, 648, 672, 696, 720 (rel intensity 100), 736 (n=1), 753 (n=2), 770 (n=3), 787 (n=4), 804 (n=5), 821 (n=6), 838 (n=7), 855 (n=8), 872 (n=9), 889 (n=10), 906 (n=11), 923 (n=12), 940 (n=13), 957 (n=14), 974 (n=15), and 991 (n=16).

EXAMPLE 7

Synthesis of Water-Soluble Poly(Sodium Sulfonylbutoxylated) Fullerene Derivatives $C_{60}$ $(OCH_2CH_2CH_2CH_2SO_3Na)_x$, or Poly(sodium Sulfonylpropoxylated) Fullerene Derivatives $C_{60}$ $(OCH_2CH_2CH_2SO_3Na)_x$ A reaction flask (100 ml) was charged with a solution of either fullerenol-2 or fullerenol-9 (500 mg) in DMF (25 ml), which was dried over molecular sieves (4 Å). To this solution was added Na metal (1.2 equiv. of hydroxy group) and the resulting mixture was stirred for 5.0 h to afford a clear brown solution of $C_{60}(ONa)_{12}$ (ave.) for fullerenol-2 and $C_{60}(ONa)_{6\ or\ 8}$ for fullerenol-9 as versatile reactive intermediates. 1,4-Butane sultone or 1,3-propane sultone (1.2 equiv. of hydroxy group) was then added and the solution was stirred at ambient temperature for 4 h. At the end of reaction, it was added methanol (80 ml) to cause the precipitation of brown solids. The solid precipitate was isolated by centrifugation. It was then washed twice with methanol (30 ml each time) and dried in vacuum at 40° C. to afford brown solids of water-soluble poly(sodium sulfonylbutoxylated), $C_{60}(OCH_2CH_2CH_2CH_2SO_3Na)_x$, or poly(sodium sulfonylpropoxylated), $C_{60}(OCH_2CH_2CH_2SO_3Na)_x$, fullerene derivatives corresponding to 1,4-butane sultone or 1,3-propane sultone used, respectively. In the reactions where fullerenol-9 and 1.2 equiv. of sultone reagent per hydroxy group were used as the reagents, the exact chemical composition of $C_{60}(OCH_2CH_2CH_2CH_2SO_3Na)_6$ or $C_{60}(OCH_2CH_2CH_2SO_3Na)_8$ was obtained.

EXAMPLE 8

Synthesis of Poly(Organoxylated) Fullerene Derivatives $C_{60}(-O-B-C-D)_x$

A reaction flask (100 ml) was charged with a solution of either fullerenol-2 or fullerenol-9 (500 mg) in DMF (25 ml), which was dried over molecular sieves (4 Å). To this solution was added Na metal (1.2 equiv. of hydroxy group) and the resulting mixture was stirred for 5.0 h to afford a clear brown solution of $C_{60}(-ONa)_{12}$ (ave.) for fullerenol-2 and $C_{60}(-ONa)_{6\ or\ 8}$ for fullerenol-9 as versatile reactive intermediates. Reagent with a reactive leaving-group such as Br—B—C—D, $CH_3SO_2O$—B—C—D, or $CF_3SO_2O$—B—C—D (1.2 equiv. of hydroxy group) was then added and the solution was stirred at ambient temperature to 70° C. for 4 h. At the end of reaction, diethyl ether (80 ml) was added to cause the precipitation of brown solids. The solid precipitate was isolated by centrifugation, and then washed twice with diethyl ether (30 ml each time) and dried in vacuum at 40° C. to afford brown solids of the corresponding poly (organoxylated), $C_{60}(-O-B-C-D)_x$, fullerene derivatives. In reactions where fullerenol-9 was sued as a reagent, the exact chemical composition of $C_{60}(-O-B-C-D)_6$ or $C_{60}(-O-B-C-D)_8$ was obtained. With the amino protecting group $-N(COCH_2)_2$, the hydroxy protecting group $-O-Si(CH_3)_3$, and the thiol protecting group $-S-CH_2-Ar$, a deprotection reaction can be carried out with $C_{60}(-O-B-C-D)_x$ to give the corresponding $-NH_2$, $-OH$, and $-SH$ end groups.

In this experiment, B and C, in combination, form a $C_6$ alkyl group, and D is OH (protected by $-N(COCH_2)_2$). However, B, C and D (properly protected, if necessary) can be any of the respective moieties assigned to them in the "Summary of the Invention" section with the exceptions of polyanhydride and polycarbonate.

EXAMPLE 9

Synthesis of Water-Soluble Poly(Sodium Sulfonylbutylated) Fullerene Derivative $C_{60}$ $(CH_2CH_2CH_2CH_2SO_3Na)_x$ or Poly(Sodium Sulfonylpropylated) Fullerene Derivative $C_{60}$ $(CH_2CH_2CH_2SO_3Na)_x$ A round-bottom reaction flask A (100 ml) equipped with a magnetic stirrer was fitted with a septum and purged with $N_2$. It was charged with fullerene (500 mg), pure $C_{60}$ or fullerene mixtures, toluene (40 ml) and 1,4-butane sultone or 1,3-propane sultone (5-20 equiv. of fullerene). The solution was dried over molecular sieves (4 Å) prior to use. In a separated flask B, naphthalene (5-20 equiv. of fullerene) dissolved in dimethoxyethane (DME, 10 ml, dried over molecular sieves 4 Å prior to use) was allowed to react with sodium (5-20 equiv. of fullerene), forming a greenish complex solution of sodium naphthalide. This sodium naphthalide solution was then added into the reaction flask A via the syringe technique. The mixture was stirred at ambient temperature for 4 h under $N_2$. At the end of reaction, it was added $H_2O$ (2 ml) to quench all reactive intermediates and the resulting solution was added into methanol (60 ml) to effect precipitation of brown solids. The solid precipitate was isolated by centrifugation. It was then washed twice with methanol (20 ml each time) and dried in vacuum at 40° C. to afford brown solids of water-soluble poly(sodium sulfonylbutylated), $C_{60}(CH_2CH_2CH_2CH_2SO_3Na)_x$, or poly (sodium sulfonylpropylated), $C_{60}(CH_2CH_2CH_2-SO_3Na)_x$, fullerene derivatives corresponding to 1,4-butane sultone or 1,3-propane sultone used, respectively. The value of x varies with the amount of sodium naphthalide used in the reaction. Infrared data of poly(sodium sulfonylalkylated) fullerene derivatives are as follow: $IRv_{max}$ (KBr) 1642, 1570, 1384, 1192, 1038, 797, 750, 603 and 534 $cm^{-1}$.

EXAMPLE 10

Synthesis of Poly(Functional Alkylated) Fullerene Derivatives $C_{60}(-CH_2-B-C-D)_x$ A round-bottom reaction flask A (100 ml) equipped with a magnetic stirrer was fitted with a septum and purged with $N_2$. It was charged with fullerene (500 mg), pure $C_{60}$ or fullerene mixtures, toluene (40 ml) and $CH_3SO_2O$—$CH_2$—B—C—D or $CF_3SO_2O$—$CH_2$—B—C—D (5-20 equiv. of fullerene). The solution was dried over molecular sieves (4 Å) prior to use. In a separated flask B, naphthalene (5-20 equiv. of fullerene) dissolved in DME (10 ml) and dried over molecular sieves (4 Å) prior to use was allowed to react with sodium (5-20 equiv. of fullerene), forming a greenish complex solution of sodium naphthalide. This sodium naphthalide solution was then added into the reaction flask A via the syringe technique. The mixture was stirred at ambient temperature for 4 h under $N_2$. At the end of reaction, it was added $H_2O$ (2 ml) to quench all reactive intermediates and the resulting solution was added into methanol (60 ml) to effect precipitation of brown solids. The solid precipitate was isolated by centrifugation. It was then washed twice with methanol (20 ml each time) and dried in vacuum at 40° C. to afford brown solids of poly(functional alkylated)

fullerene derivatives $C_{60}(-CH_2-B-C-D)_x$. The value of x varies with the amount of sodium naphthalide used in the reaction. With the amino protecting group $-N(COCH_2)_2$, the hydroxy protecting group $-O-Si(CH_3)_3$, and the thiol protecting group $-S-CH_2-Ar$, a deprotection reaction can be carried out with $C_{60}(-O-B-C-D)_x$ to give the corresponding $-NH_2$, $-OH$, and $-SH$ end groups.

In this experiment, B and C, in combination, form a $C_6$ alkyl group, and D is OH (protected by $-N(COCH_2)_2$). However, B can be any of the following: $-R-O-[Si(CH_3)_2-O-]_{1-100}$, $C_{1-2000}$ alkyl, $C_{6-40}$ aryl, $C_{7-60}$ alkylaryl, $C_{7-60}$ arylalkyl, $(C_{2-30}$ alkyl ether$)_{1-100}$, $(C_{6-40}$ aryl ether$)_{1-100}$, $(C_{7-60}$ alkylaryl ether$)_{1-100}$, $(C_{7-60}$ arylalkyl ether$)_{1-100}$, $(C_{2-30}$ alkyl thioether$)_{1-100}$, $(C_{6-40}$ aryl thioether$)_{1-100}$, $(C_{7-60}$ alkylaryl thioether$)_{1-100}$, $(C_{7-60}$ arylalkyl thioether$)_{1-100}$. C can be any of the following: $-R-$, $-R-Ar-$, $-Ar-R-$, or $-Ar-$. D (properly protected, if necessary) can be any of the following: $-H$, $-O-Si(CH_3)_3$, $-S-CH_2-Ar$, $-SO_3^-$, $-OSO^{3-}$, $-CO^{2-}$, $-PO^{3-}$, $-O-PO(O^-)-O-PO_3^{-2}$, $-O-PO_3^{-2}$, $-O-PO(O^-)-O-PO(O^-)-O-PO_3^{-2}$, $-N(COCH_2)_2$, or $-NR_1R_2$, each of R, $R_1$, and $R_2$ being independently $C_{1-20}$ alkyl and Ar being aryl.

EXAMPLE 11

Synthesis of Hexamino Fullerene Derivatives $C_{60}$ $(-NH_2)_6$, Octamino Fullerene Derivatives $C_{60}(-NH_2)_8$, and Tetracosaamino Fullerene Derivatives $C_{60}(-NH_2)_{24}$ (Fullerenamines)

A round-bottom reaction flask (100 ml) equipped with a magnetic stirrer was fitted with a septum and a cool-trap condenser. It was charged with either hexabromo-$C_{60}$ fullerene (500 mg; see Birkett, et al., Nature 1992, 357, 479), hexachloro-$C_{60}$ fullerene (500 mg; see Birkett, et al., Chem. Soc., Chem. Commun. 1993, 1230), octabromo-$C_{60}$ fullerene (500 mg; see Birkett, et al., Nature 1992, 357, 479) or tetracosabromo-$C_{60}$ fullerene (500 mg; see Tebbe, et al., Science 1992, 256, 822), DMF (20 ml) and 4-dimethylamino-pyridine or 1,8-diazabicyclo[5.4.0]undec-7-ene (DBU, 450 mg). The solution was slowly bubbled with $NH_3$ gas (20 ml per min) at 60° C. for 7 h with the dry-ice/acetone filling in the cool-trap. At the end of reaction, the resulting solution was added methanol (60 ml) to effect precipitation of brown solids. The solid precipitate was isolated by centrifugation. It was then washed twice with methanol (20 ml each time) and dried in vacuum at 40° C. to afford brown solid of the corresponding hexamino fullerene derivative $C_{60}(NH_2)_6$, octamino fullerene derivative $C_{60}(NH_2)_8$, or tetracosamino fullerene derivative $C_{60}(NH_2)_{24}$. Fullerenamines of $C_{60}(NH_2)_6$ and $C_{60}(NH_2)_8$ have appreciable solubility in DMF and $C_{60}(NH_2)_{24}$ is soluble in water.

EXAMPLE 12

Synthesis of Hexamino Fullerene Derivatives $C_{60}$ $(-NH_2)_6$, Octamino Fullerene Derivatives $C_{60}(-NH_2)_8$, and Tetracosaamino Fullerene Derivatives $C_{60}(-NH_2)_{24}$ (Fullerenamine)

A round-bottom reaction flask A (100 ml) equipped with a magnetic stirrer was fitted with a septum and purged with $N_2$. It was charged with either hexabromo-$C_{60}$ fullerene (500 mg; see Birkett, et al., Nature 1992, 357, 479), hexachloro-$C_{60}$ fullerene (500 mg; see Birkett, et al., Chem. Soc., Chem. Commun. 1993, 1230), octabromo-$C_{60}$ fullerene (500 mg; see Birkett, et al., Nature 1992, 357, 479) or tetracosabromo-$C_{60}$ fullerene (500 mg; see Tebbe, et al., Science 1992, 256, 822) and DMF (20 ml). In a separated reaction flask B, benzamide (1.1 equiv. of halogen group in halogenated fullerene) was allowed to react with sodium hydride (1.1. equiv. of benzamide) in THF (20 ml, distilled over Na) at ambient temperature to afford immediately the corresponding solution of sodium benzamide ($C_6H_5CONHNa$). The solution was added portionwise into the reaction flask A at 0° C. and the mixture was stirred further at that temperature for an additional 3 h. At the end of reaction, all solvents were removed from the resulting solution in vacuum to give brown solids. These solids were transferred into an aqueous solution of NaOH (15 ml, 3N) and the mixture was stirred and heated at 90° C. for 16 h. It was cooled to ambient temperature and added methanol (60 ml) to cause precipitation of dark brown solids. The solid precipitate was isolated by centrifugation. It was then washed twice with methanol (20 ml each time) and dried in vacuum at 40° C. to afford brown solid of the corresponding hexamino fullerene derivative $C_{60}(NH_2)_6$, octamino fullerene derivative $C_{60}(NH_2)_8$, or tetracosamino fullerene derivative $C_{60}(NH_2)_{24}$.

EXAMPLE 13

Synthesis of Functionalized Hexaorgano Fullerene Derivatives $C_{60}(-A-B-C-D)_6$, Octaorgano Fullerene Derivatives $C_{60}(-A-B-C-D)_8$, and Tetracosaorgano Fullerene Derivatives $C_{60}(-A-B-C-D)_{24}$ A round-bottom reaction flask (100 ml) equipped with a magnetic stirrer was fitted with a septum and purged with $N_2$. It was charged with either hexabromo-$C_{60}$ fullerene (500 mg; see Birkett, et al., Nature 1992, 357, 479), hexachloro-$C_{60}$ fullerene (500 mg; see Birkett, et al., Chem. Soc., Chem. Commun. 1993, 1230), octabromo-$C_{60}$ fullerene (500 mg; see Birkett, et al., Nature 1992, 357, 479) or tetracosabromo-$C_{60}$ fullerene (500 mg; see Tebbe, et al., Science 1992, 256, 822), THF (20 ml, distilled over Na) and 4-dimethylaminopyridine or DBU (450 mg). It was added either HO—B—C—D, $H_2N$—B—C—D, or HS—B—C—D (1.3 equiv. of halogen group in halogenated fullerene) and the mixture was stirred and heated at 70° C. for 16 h. At the end of reaction, THF was evaporated from the resulting solution to afford pale brown to brown solids. The solid was added into water (30 ml) with stirring to give fine suspension of products. The solid precipitate was isolated by centrifugation. It was then washed twice with water (20 ml each time), twice with diethyl ether (20 ml each time), and dried in vacuum at 40° C. to afford pale brown to brown solids of the corresponding functionalized hexaorgano fullerene derivatives $C_{60}(-A-B-C-D)_6$, octaorgano fullerene derivatives $C_{60}(-A-B-C-D)_8$, and tetracosaorgano fullerene derivatives $C_{60}(-A-B-C-D)_{24}$.

In this experiment A is $-O-$, B and C in combination form $C_6$ alkyl, and D is $-OH$ and $-O-Si(CH_3)_3$. However, B, C and D (properly protected, if necessary) can be any of the respective moieties assigned to them in the "Summary of the Invention" section.

EXAMPLE 14

Synthesis of Polyamino Fullerene Derivatives, $C_{60}$ $(-NH_2)_n$ (Fullerenamine)

A two-necked reaction flask A (50 mL) was equipped with a vertical dropping funnel with a stopcock on one neck and a connecting gas bubbling tube on the other neck. The gas-bubbling tube was attached with a drying tube ($CaCl_2$) and inserted into the second two-necked reaction flask B. The other neck of flask B was attached with a bubbling tube which was extended into a trapping flask containing aqueous sodium hydroxide solution (2N). To minimize the back-flow of moisture from alkaline solution, a drying tube ($CaCl_2$) was installed in between the flask B and the trapping flask. A steady inert gas ($N_2$) flow was allowed starting from the top of dropping funnel, through the reaction flasks A and B in sequence, into the alkaline solution in the trapping flask. The dropping funnel and the reaction flask A were charged with conc. $HNO_3$ (10 mL) and copper powder (10 g) or sodium nitrite ($NaNO_2$, 10 g), respectively. In the reaction flask B was placed a solution of $C_{60}$ fullerene (500 mg) in benzene (50 mL, dried over Na). The inert gas bubbling through the $C_{60}$ solution in the flask B was adjusted to a flow rate of 5 mL per min. The fullerene solution was deoxygenated for at least 5 min prior to the reaction. Conc. $HNO_3$ solution was then allowed to add dropwise into sodium nitrite solids in the flask A. Brown fume was produced immediately upon the contact of conc. $HNO_3$ with $NaNO_2$. It was carried by the steady flow of $N_2$ and bubbled through the $C_{60}$ solution in the flask B. Within 15 min of reaction, the purple solution of $C_{60}$ was changed to orange-red progressively. The mixture was stirred at ambient temperature for an additional 2 h to give a dark brown-red solution with suspended solids. At the end of reaction, excessive nitrogen dioxide ($NO_2$) was removed by $N_2$ bubbling and destroyed in the trapping solution. Benzene was then evaporated from the product solution at a reduced pressure to give dark brown solids. The solids were suspended in anhydrous n-hexane, separated from n-hexane solution by centrifugation and dried in vacuum at 40° C. to afford brown solids of polynitro fullerene derivatives, $C_{60}(NO_2)_n$ (n=12 on average) (650 mg). $IRv_{max}$ (KBr) 1572 [s, $v_{as}$(N—O)], 1328 [s, $v_s$(N—O)], 1085, 1038, 973, 815 (δ), 760, 733, 696, 545, and 466. Polynitro compound exhibits appreciable solubility in common organic solvents such as THF, DMF, $CH_2Cl_2$, $CH_3OH$ and DMSO.

A round-bottom reaction flask (100 ml) equipped with a magnetic stirrer was fitted with a septum and a cool-trap condenser. It was charged with polynitro fullerene derivatives, $C_{60}(NO_2)_n$, (500 mg), DMF (20 ml) and 4-dimethylaminopyridine or DBU (450 mg). The solution was slowly bubbled with $NH_3$ gas (20 ml per min) at 60° C. for 7 h with the dry-ice/acetone filling in the cool-trap. At the end of reaction, the resulting solution was added methanol (60 ml) to effect precipitation of brown solids. The solid precipitate was isolated by centrifugation. It was then washed twice with methanol (20 ml each time) and dried in vacuum at 40° C. to afford brown solid of the corresponding polyamino fullerene derivative $C_{60}(NH_2)_n$ (n=16 on average). The increase of n is due to the further slow nucleophilic addition of $NH_3$ on polyaminated fullerenes under basic conditions. Therefore, the increase is time and pH dependent.

EXAMPLE 15

Synthesis of Polyamino Fullerene Derivatives, $C_{60}(—NH_2)_n$ (Fullerenamine)

A round-bottom reaction flask (100 ml) equipped with a magnetic stirrer was fitted with a septum and a cool-trap condenser. It was charged with polynitro fullerene derivatives, $C_{60}(NO_2)_n$, synthetically described in Example 14 (500 mg) and DMF (20 ml). The solution was added $NaNH_2$ (400 mg) and stirred at 60° C. for 7 h. At the end of reaction, the resulting solution was added methanol (60 ml) to effect precipitation of brown solids. The solid precipitate was isolated by centrifugation. It was then washed twice with methanol (20 ml each time) and dried in vacuum at 40° C. to afford brown solid of the corresponding polyamino fullerene derivative $C_{60}(—NH_2)_n$.

EXAMPLE 16

Synthesis of Polyamino Fullerene Derivatives, $C_{60}(—NH_2)_n$ (Fullerenamine)

A round-bottom reaction flask A (100 ml) equipped with a magnetic stirrer was fitted with a septum and purged with $N_2$. It was charged with polynitro fullerene derivatives, $C_{60}(NO_2)_n$, synthetically described in Example 14 (500 mg) and DMF (20 ml). In a separated reaction flask B, benzamide (1.1 equiv. of halogen group in halogenated fullerene) was allowed to react with sodium hydride (1.1. equiv. of benzamide) in THF (20 ml, distilled over Na) at ambient temperature to afford immediately the corresponding solution of sodium benzamide ($C_6H_5CONHNa$). The solution was added portionwise into the reaction flask A at 0° C. and the mixture was stirred further at that temperature for an additional 3 h. At the end of reaction, all solvents were removed from the resulting solution in vacuum to give brown solids. These solids were transferred into an aqueous solution of NaOH (15 ml, 3N) and the mixture was stirred and heated at 90° C. for 16 h. It was cooled to ambient temperature and added methanol (60 ml) to cause precipitation of dark brown solids. The solid precipitate was isolated by centrifugation. It was then washed twice with methanol (20 ml each time) and dried in vacuum at 40° C. to afford brown solids of the corresponding polyamino fullerene derivative, $C_{60}(NH_2)_n$ where n is about 8 (averaged).

EXAMPLE 17

Synthesis of Functionalized Polyorgano Fullerene Derivatives, $C_{60}(—A—B—C—D)_n$ A round-bottom reaction flask (100 ml) equipped with a magnetic stirrer was fitted with a septum and purged with $N_2$. It was charged with polynitro fullerene derivatives, $C_{60}(NO_2)_n$, synthetically described in Example 14 (500 mg), THF (20 ml, distilled over Na) and 4-dimethylaminopyridine or DBU (450 mg). It was added either HO—B—C—D, $H_2N$—B—C—D, or HS—B—C—D (1.3 equiv. of halogen group in halogenated fullerene) and the mixture was stirred and heated at 70° C. for 16 h. At the end of reaction, THF was evaporated from the resulting solution to afford pale brown to brown solids. The solid was added into water (30 ml) with stirring to give fine suspension of products. The solid precipitate was isolated by centrifugation. It was then washed twice with water (20 ml each time), twice with diethyl ether (20 ml each time), and dried in vacuum at 40° C. to afford pale brown to brown solids of the corresponding functionalized polyorgano fullerene derivatives, $C_{60}(—A—B—C—D)_n$ where n is about 8 (averaged).

In this experiment A is —O—, B and C in combination form $C_6$ alkyl, and D is —OH. However, B, C and D (properly protected, if necessary) can be any of the respective moieties assigned to them in the "Summary of the Invention" section.

EXAMPLE 18

Synthesis of Polyamino Fullerene Derived Compounds, $C_{60}(—NH—CO—NH—B—C—D)_x$

A reaction flask (100 ml) is charged with a solution of either polyamino fullerenes [fullerenamines from Example 14–16, $C_{60}(-NH_2)_n$, 500 mg], hexamino fullerene [$C_{60}(-NH_2)_6$, from Example 11 or 12,500 mg], octamino fullerene [$C_{60}(-NH_2)_8$, from Example 11 or 12,500 mg], or tetracosaamino fullerene [$C_{60}(-NH_2)_{24}$, from Example 11 or 12,500 mg] in dimethyl formamide (25 ml), which is dried over molecular sieves (4 Å). To this solution is added an organic reagent of OCN—B—C—D (1.2 equiv of each amino group used) containing a reactive isocyanate function. The solution is stirred at ambient temperature to 60° C. for 4 h. At the end of the reaction period, diethyl ether (80 ml) is added to cause the precipitation of brown solids. The solid precipitates are isolated by centrifugation. It is then washed twice with diethyl either (30 ml each time) and dried in vacuum at 40° C. to afford brown solids of the corresponding fullerenic poly(organo-urea), $C_{60}(-NH-CO-NH-B-C-D)_n$. In reactions using hexamino fullerene, octamino fullerene, or testracosaamino fullerene as a starting reagent, the exact chemical composition of $C_{60}(-NH-CO-NH-B-C-D)_6$, $C_{60}(-NH-CO-NH-B-C-D)_8$, or $C_{60}(-NH-CO-NH-B-C-D)_{24}$ is obtained, respectively. With the amino protecting group —N(CO $CH_2)_2$, the hydroxy protecting group —O—$Si(CH_3)_3$, and the thiol protecting group —S—$CH_2$—Ar, a deprotection reaction can be carried out with $C_{60}(-O-B-C-D)_x$ to give the corresponding —$NH_2$, —OH, and —SH end groups. B, C and D (properly protected, if necessary) can be any of the respective moieties assigned to them in the "Summary of the Invention" section.

EXAMPLE 19

Synthesis of Polyamino Fullerene Derived Compounds, $C_{60}(-NH-CO-B-C-D)_x$

Synthesis of Polyamino Fullerene Derived Compounds, $C_{60}(-NH-CO-B-C-D)_x$. A reaction flask (100 ml is charged with a solution of either polyamino fullerenes [fullerenamines from Example 14–16, $C_{60}(-NH_2)_n$, 500 mg], hexamino fullerene [$C_{60}(-NH_2)_6$, from Example 11 or 12,500 mg], octamino fullerene [$C_{60}(-NH_2)_8$, from Example 11 or 12,500 mg], or tetracosaamino fullerene [$C_{60}(-NH_2)24$, from Example 11 or 12,500 mg] in dimethyl formamide (25 ml), which is dried over molecular sieves (4 Å). To this solution is added an organic acid chloride reagent of Cl—CO—B—C—D (1.2 equiv of each amino group used) containing a highly reactive acid chloride function and triethylamine (dried over molecular sieves, 600 mg). The solution is stirred at ambient temperature to 70° C. for 8 h. At the end of the reaction period, dichloromethane (80 ml) is added to cause the precipitation of brown solids. The solid precipitates are isolated by centrifugation. It is then washed twice with dichloromethane (30 ml each time) and dried in vacuum at 40° C. to afford brown solids of the corresponding fullerenic poly(organo-amide), $C_{60}(-NH-CO-B-C-D)_n$. In reactions using hexamino fullerene, octamino fullerene, or tetracosaamino fullerene as a starting reagent, the exact chemical composition of $C_{60}(-NH-CO-B-C-D)_6$, $C_{60}(-NH-CO-B-C-D)_8$, or $C_{60}(-NH-CO-B-C-D)_{24}$ is obtained, respectively. With the amino protecting group —N(COCH$_2$)$_2$, the hydroxy protecting group —O—$Si(CH_3)_3$, and the thiol protecting group —S—$CH_2$—Ar, a deprotection reaction can be carried out with $C_{60}(-O-B-C-D)_x$ to give the corresponding —$NH_2$, —OH, and —SH end groups. B, C and D (properly protected, if necessary) can be any of the respective moieties assigned to them in the "Summary of the Invention" section.

EXAMPLE 20

Detection of Superoxide Radicals in Whole Blood

Biological evaluations of water-soluble fullerenol-1 as a free-radical scavenger were performed on heparinized whole blood samples from different patients (both males and females of different ages) with acute pancreatitis, gastric cancer, breast cancer, or gastric ulcer. The whole blood samples used in the study were acquired from patients in the early morning after 12 hrs of fasting. The heparinized blood (treated by mucopolysaccharide acid) was wrapped immediately with aluminum foil to minimize possible light exposure and kept at 5° C. prior to the testing within approximately 2 h. In each measurement, heparinized blood (0.2 ml) placed inside a stainless cell (5 cm in diameter) in an absolutely dark chamber of a chemiluminescence analyzing system was charged with phosphate-buffered solution (PBS; 0.1 ml, pH 7.4). Photon emission from the whole blood was counted at an interval of 10 sec at 37° C. under atmospheric conditions. After a period of 200 sec, a chemiluminigenic compound lucigenin (i.e., bis-N-methylacridinium nitrate; 1.0 ml, 0.01 mM) in PBS buffer solution was injected into the cell and the chemiluminescence emitted from the blood sample was continuously measured for an additional period of 400 sec. In the study, the total count of chemiluminescence was calculated by integrating the area under the chemiluminescence-vs-time curve and then subtracting it from the background level. Note that in control experiments, superoxide dismutase was found to decrease chemiluminescence intensity, indicating the existence of superoxide radicals in the blood samples.

Referring to FIG. 1, a whole blood sample from a male patient with acute pancreatitis (age 60) showed the chemiluminescence intensity level of 2888 counts/10 sec after the addition of lucigenin. When a whole blood sample from the same patient was pre-treated with fullerenol-1 at a concentration of 60 µg/ml, a much lower chemiluminescence intensity level, i.e., 397 counts/10 sec, was observed, indicating that fulerenol-1 has a free-radical scavenging efficiency of 86.3%. More results from other patients with acute pancreatitis, breast cancer, and gastric cancer are listed in the table below:

| Disease | Sex | Age | F* | Counts+ | Decrease (%) |
| --- | --- | --- | --- | --- | --- |
| Acute pancreatitis | F | 60 | 0 | 648.2 | |
| | | | 60 | 306.5 | 52.7 |
| Acute pancreatitis | M | 60 | 0 | 2887.9 | |
| | | | 60 | 397.0 | 86.3 |
| Acute pancreatitis | F | 42 | 0 | 4945.9 | |
| | | | 80 | 1206.7 | 75.6 |
| Acute pancreatitis | F | 42 | 0 | 7157.8 | |
| | | | 60 | 1275.4 | 82.2 |
| | | | 80 | 1335.0 | 81.4 |
| Acute pancreatitis | M | 60 | 0 | 5802.3 | |
| | | | 60 | 1508.1 | 74.0 |
| Acute pancreatitis | M | 78 | 0 | 2167.3 | |
| | | | 60 | 1139.3 | 47.4 |
| | | | 80 | 618.7 | 71.5 |
| Breast cancer | F | 38 | 0 | 1537.7 | |
| | | | 60 | 596.6 | 61.2 |
| Gastric ulcer | M | 67 | 0 | 741.7 | |
| | | | 60 | 576.9 | 22.2 |
| Gastric cancer | M | 69 | 0 | 2601.2 | |
| | | | 60 | 575.5 | 77.9 |
| Gastric cancer | F | 72 | 0 | 1679.7 | |
| | | | 10 | 948.4 | 43.5 |
| Gastric cancer | F | 56 | 0 | 1237.0 | |
| | | | 60 | 182.4 | 85.3 |

*Fullerenol-1 in µg/ml
+Counts in 10 seconds

EXAMPLE 21

Measurement of Radical Scavenging Activity in Vascular Rings

The measurement of superoxide production in vascular rings was performed according to a method modified from that reported by Heim, et al., J. Pharmaocl. Exp. Ther. 1991, 256, 537. More specifically, vascular rings were incubated at 37° C. under 5% $CO_2$ in $O_2$. The diabetogenic drug alloxan, a stimulant for the production of $O_2.^-$. was introduced into the incubation medium followed immediately by the addition of Cytochrome C (37.5M), the reduction of which is known to be induced by superoxide radical. At the end of incubation period, N-ethylmaleimide (3 mM) was added to prevent further reduction of cytochrome C. These steps were repeated as a sequential test with intermediate rinsings with a buffer solution. To ensure that $O_2.^-$ was responsible for the reduction of cytochrome C, some samples were incubated in the presence of superoxide dismutase. As a result, a complete inhibition of cytochrome C reduction upon addition of superoxide dismutase was observed, indicating a correlation between $O_2.^-$ and cytochrome C. The quantity of reduced cytochrome containing a low oxidation state of iron ($Fe^{+2}$) was detected and calculated by the extinction coefficient of its specific optical absorption at $\lambda=550$ nm. After the test, each vascular ring was opened and the area of endothelial surface was measured. Thus, the quantity of $O_2.^-$ produced in the test can be expressed in nmol per $cm^2$ per min.

When evaluating the free radical-scavenging efficiency of fullerenol-1 or fullerenol-2, the vascular ring was allowed to contact with the fullerenol for at least 10 min prior to the addition of alloxan. The alloxan-stimulated production of $O_2.^-$ from intact vascular rings follows a dose-dependent relationship. It was found that a suitable concentration of alloxan (10 mM) significantly increased the production of $O_2.^-$ to a level of 326.8±36.6 nmol/cm2/min (n=5). The production of $O_2.^-$ was then gradually depressed by the pre-treatment of vascular rings with the fullerenol at a concentration of $10^{-6}$, $10^{-5}$ and $10^{-4}$M. Such results indicate that the fullerenol acted as a superoxide radical scavenger in vascular rings.

EXAMPLE 22

Antiproliferative Activities

The antiproliferative activities of both fullerenol-1 and fullerenol-2 were measured as their ability to inhibit the proliferation of cultured rabbit aortic smooth muscle cells induced by the fetal calf serum. See Huang, Et al., Eur. J. Pharmacol. 1992, 221, 381. More specifically, the intima and inner two-thirds of the cell-containing media were removed from the isolated rabbit aorta in strips of 1 mm in width. The strips were further cut into square pieces and placed in a dry petri dish. The dish was then filled with the DMEM medium supplemented with 10% fetal calf serum. When the cells approached confluence, the aorta pieces were removed. Cells between passages 3 and 8 were used, and their viability was determined by the trypan blue dye exclusion method. The proliferative response of vascular smooth muscle cells was determined based on the uptake of tritiated thymidine for DNA synthesis. Prior to all experiments, confluent smooth muscle cells ($2.5\times10^4$ cells/well) were rendered quiescent by culturing for 48 h in 0.5% fetal calf serum. The medium was then charged with stimulator, i.e., 5% fetal calf serum, and the fullerenol. The resulting mixture was kept for 24 h before the subsequent addition of [$^3$H]thymidine (0.2 Ci/well). After an additional twenty-four hr of culturing, the cells were harvested and the incorporated [$^3$H]thymidine was counted by a liquid scintillation counter. Each experiment was performed in triplicate.

Figure 2:
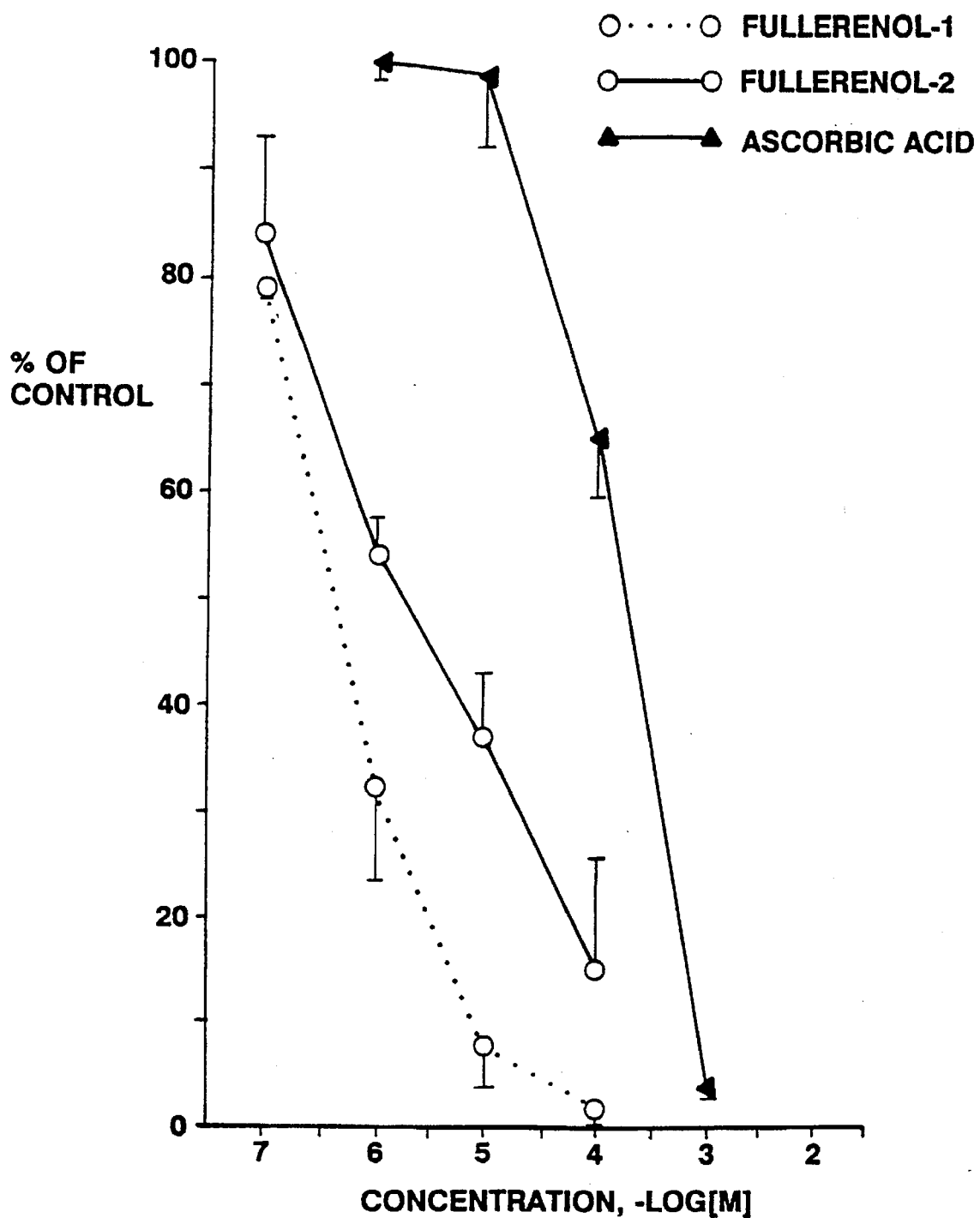
FIG. 2 is a graph showing the effect of two fullerenols on the proliferative response of rabbit vascular smooth muscle cells.

The inhibitory activities of fullerenol-1 and fullerenol-2 were expressed as percentages of the untreated control value obtained upon addition of stimulator under similar conditions in the absence of fullerenols. The concentration evoking 50% of the maximal inhibition ($IC_{50}$) was calculated accordingly for each experiment. The control value for the incorporation of [$^3$H]thymidine in proliferative cultures of rabbit vascular smooth muscle cells, induced by 5% fetal calf serum, was found to be 12527±2011 cpm/well. Exposure of smooth muscle cells to fullerenols, in a dose range of $10^{-7}$ to $10^{-4}$M, inhibited significantly the incorporation of [$^3$H]thymidine. As shown in FIG. 2, a sharp decrease of proliferative response was observed as the dose concentrations increased. The $IC_{50}$ values (n=7) were determined to be 0.30±0.07 µM for fullerenol-1 and 2.2±0.5 µM for fullerenol-2. The maximal inhibitory activities of water-soluble fullerenols at a dose level of $10^{-4}$M were found to be 98.0±1.7% for fullerenol-1 and 87.0±9.8% for fullerenol-2. Comparison of these data with the inhibitory activities of ascorbic acid (vitamin C) shows that it requires more than 130 times as much ascorbic acid as fullerenol-1 to achieve 50% inhibition of the proliferative activities. These results demonstrated, for the first time, that water-soluble fullerenols exhibited the antiproliferative effects on rabbit vascular smooth muscle cells.

Much higher antiproliferative activities of fulerenol-1 and fulerenol-2, as compared with ascorbic acid, were also observed with human T-lymphoid leukemia CEM cells (obtained from the American Type Culture Collection, Rockville, Md.). More specifically, $IC_{50}$ values (n=5) of fullerenol-1 and fullerenol-2 were determined to be 3.5±0.6 µM and 4.3±0.8 µM. Indeed, the $IC_{50}$ value of fullerenol-1 is 60 times that of ascorbic acid. The maximal inhibitory activities of fullerenol-1 and fullerenol-2 were found to be 86.0±3.1% and 87.0±3.0%, respectively.

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. For example, counter ionic salts, if any, of the fullerene derivatives described above and their use are within the scope of this invention. As another example, while only fullerene derivatives containing poly(simple ether) substituents are described herein, fullerene derivatives containing poly (mixed ether) substituents, either by themselves or as components of compositions, are also covered by this invention under the doctrine of equivalents. Thus, other embodiments are also within the claims.

What is claimed is:

1. A compound of the following formula:

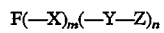

wherein

F is a fullerene core;

each X is independently —$CO_2^-$, —$SO_3^-$, —SH, —$PO_3^-$, —O—$PO_3^{-2}$, —O—PO($O^-$)—O—$PO_3^{-2}$, —O—PO($O^-$)—O—PO($O^-$)—O—$PO_3^{-2}$, or —O—PO($O^-$)—O—$CH_2$—$CH_2$—$NH_3^+$;

each Y is —A—B—, in which A is independently —$CH_2$—, —O—, —S—, —NH—CO—NH—, or —NH—CO—; and B is independently —$R_a$—O—[Si($CH_3$)$_2$—O—]$_{1-100}$, $C_{1-2000}$ alkyl, $C_{6-40}$ aryl, $C_{7-60}$ alkylaryl, $C_{7-60}$ arylalkyl, ($C_{1-30}$ alkyl ether)$_{1-100}$, ($C_{6-40}$ aryl ether)$_{1-100}$, ($C_{7-60}$ alkylaryl ether)$_{1-100}$, ($C_{7-60}$ arylalkyl ether)$_{1-100}$, ($C_{1-30}$ alkyl thioether)$_{1-100}$, ($C_{6-40}$ aryl thioether)$_{1-100}$, ($C_{7-60}$ alkylaryl thioether)$_{1-100}$, (C$_{7-60}$ arylalkyl thioether)$_{1-100}$, (C$_{2-50}$ alkyl ester)$_{1-100}$, (C$_{7-60}$ aryl ester)$_{1-100}$, (C$_{8-70}$ alkylaryl ester)$_{1-100}$, (C$_{8-70}$ arylalkyl ester)$_{1-100}$, —R—CO—O—(C$_{1-30}$ alkyl ether)$_{1-100}$, —R—CO—O—(C$_{6-40}$ aryl ether)$_{1-100}$, —R—CO—O—(C$_{7-60}$ alkylaryl ether)$_{1-100}$, —R—CO—O—(C$_{7-60}$ arylalkyl ether)$_{1-100}$, (C$_{4-50}$ alkyl urethane)$_{1-100}$, (C$_{14-60}$ aryl urethane)$_{1-100}$, (C$_{10-80}$ alkylaryl urethane)$_{1-100}$, (C$_{10-80}$ arylalkyl urethane)$_{1-100}$, (C$_{5-50}$ alkyl urea)$_{1-100}$, (C$_{14-60}$ aryl urea)$_{1-100}$, (C$_{10-80}$ alkylaryl urea)$_{1-100}$, (C$_{10-80}$ arylalkyl urea)$_{1-100}$, (C$_{2-50}$ alkyl amide)$_{1-100}$, (C$_{7-60}$ aryl amide)$_{1-100}$, (C$_{8-70}$ alkylaryl amide)$_{1-100}$, (C$_{8-70}$ arylalkyl amide)$_{1-100}$, (C$_{3-30}$ alkyl anhydride)$_{1-100}$, (C$_{8-50}$ aryl anhydride)$_{1-100}$, (C$_{9-60}$ alkylaryl anhydride)$_{1-100}$, (C$_{9-60}$ arylalkyl anhydride)$_{1-100}$, (C$_{2-30}$ alkyl carbonate)$_{1-100}$, (C$_{7-50}$ aryl carbonate)$_{1-100}$, (C$_{8-60}$ alkylaryl carbonate)$_{1-100}$, (C$_{8-60}$ arylalkyl carbonate)$_{1-100}$, —R$_1$—O—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$, —R$_1$—O—CO—NH—(R$_2$ or Ar—R$_2$—Ar)—NH—CO—O—(C$_{2-50}$ alkyl ester, C$_{7-60}$ aryl ester, C$_{8-70}$ alkylaryl ester, or C$_{8-70}$ arylalkyl ester)$_{1-100}$, —R$_1$—O—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$—CO—NH—(R$_2$ or Ar—R$_2$—Ar)—NH—CO—O—, —R$_1$—O—CO—NH—(R$_2$ or Ar—R$_2$—Ar)—NH—CO—O—(C$_{2-50}$ alkyl ester, C$_{7-60}$ aryl ester, C$_{8-70}$ alkylaryl ester, or C$_{8-70}$ arylalkyl ester)$_{1-100}$—R$_3$—O—CO—NH—(R$_2$ or Ar—R$_2$—Ar)—NH—CO—O—, —R$_1$—NH—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$, —R$_1$—NH—CO—NH—(R$_2$ or Ar—R$_2$—Ar)—NH—CO—O—(C$_{2-50}$ alkyl ester, C$_{7-60}$ aryl ester, C$_{8-70}$ alkylaryl ester, or C$_{8-70}$ arylalkyl ester)$_{1-100}$, —R$_1$—NH—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$—CO—NH—(R$_2$ or Ar—R$_2$—Ar)—NH—CO—O—, —R$_1$—NH—CO—NH—(R$_2$ or Ar—R$_2$—Ar)—NH—CO—O—(C$_{2-50}$ alkyl ester, C$_{7-60}$ aryl ester, C$_{8-70}$ alkylaryl ester, or C$_{8-70}$ arylalkyl ester)$_{1-100}$—R$_3$—O—CO—NH—(R$_2$ or Ar—R$_2$—Ar)—NH—CO—O—, —R$_1$—O—CO—NH—(R$_2$ or Ar—R$_2$—Ar)—NH—CO—NH—(C$_{2-50}$ alkyl amide, C$_{7-60}$ aryl amide, C$_{8-70}$ alkylaryl amide, or C$_{8-70}$ arylalkyl amide)$_{1-100}$, or —R$_1$—NH—CO—NH—(R$_2$ or Ar—R$_2$—Ar)—NH—CO—NH—(C$_{2-50}$ alkyl amide, C$_{7-60}$ aryl amide, C$_{8-70}$ alkylaryl amide, or C$_{8-70}$ arylalkyl amide)$_{1-100}$;

each Z is —C—D, wherein C is independently —R—, —R—Ar—, —Ar—, or —Ar—R—; and D is independently —OH, —SH, —SO$_3^-$, —OSO$_3^-$, —CO$_2^-$, —PO$_3^-$, —O—PO$_3^{-2}$, —O—PO(O$^-$)—O—PO$_3^{-2}$, —O—PO(O$^-$)—O—PO(O$^-$)O—PO$_3^{-2}$, —O—PO(O$^-$)—O—CH$_2$—CH$_2$—NH$_3^+$, —NH$_2$, —NH$_3^+$, —N$^+$H$_2$R$_a$, —N$^+$HR$_a$R$_c$, or —N$^+$R$_a$R$_b$R$_d$; and m is 0–30, n is 0–30, and the sum of m and n is 2–30;

in which each of R, R$_1$, R$_2$, R$_3$, R$_a$, R$_b$, R$_c$, and R$_d$ is independently C$_{1-20}$ alkyl, and Ar is independently C$_{6-40}$ aryl.

2. The compound of claim 1, wherein each X is independently —CO$_2^-$, —SO$_3^-$, —PO$_3^-$, —O—PO$_3^{-2}$, —O—PO(O$^-$)—O—PO$_3^{-2}$, or —O—PO(O$^-$)—O—PO(O$^-$)—O—PO$_3^{-2}$, —O—PO(O$^-$)—O—CH$_2$—CH$_2$—NH$_3^+$;

B is independently —R$_a$—O—[Si(CH$_3$)$_2$—O—]$_{1-100}$, C$_{1-2000}$ alkyl, C$_{6-40}$ aryl, C$_{7-60}$ alkylaryl, C$_{7-60}$ arylalkyl, (C$_{1-30}$ alkyl ether)$_{1-100}$, (C$_{7-60}$ alkylaryl ether)$_{1-100}$, (C$_{1-30}$ alkyl thioether)$_{1-100}$, (C$_{7-60}$ alkylaryl thioether)$_{1-100}$, (C$_{2-50}$ alkyl ester)$_{1-100}$, (C$_{8-70}$ alkylaryl ester)$_{1-100}$, —R—CO—O—(C$_{1-30}$ alkyl ether)$_{1-100}$, —R—CO—O—(C$_{7-60}$ alkylaryl ether)$_{1-100}$, (C$_{4-50}$ alkyl urethane)$_{1-100}$, (C$_{10-80}$ alkylaryl urethane)$_{1-100}$, (C$_{5-50}$ alkyl urea)$_{1-100}$, (C$_{10-80}$ alkylaryl urea)$_{1-100}$, (C$_{2-50}$ alkyl amide)$_{1-100}$, (C$_{8-70}$ alkylaryl amide)$_{1-100}$, (C$_{3-30}$ alkyl anhydride)$_{1-100}$, (C$_{9-60}$ alkylaryl anhydride)$_{1-100}$, (C$_{2-30}$ alkyl carbonate)$_{1-100}$, (C$_{8-60}$ alkylaryl carbonate)$_{1-100}$, —R$_1$—O—CO—NH—(R$_2$ or Ph—R$_2$—Ph)—NH—CO—O—(C$_{1-30}$ alkyl ether or C$_{7-60}$ alkylaryl ether)$_{1-100}$, —R$_1$—O—CO—NH—(R$_2$ or Ph—R$_2$—Ph)—NH—CO—O—(C$_{2-50}$ alkyl ester or C$_{8-70}$ alkylaryl ester)$_{1-100}$, —R$_1$—O—CO—NH—(R$_2$ or Ph—R$_2$—Ph)—NH—CO—O—(C$_{1-30}$ alkyl ether or C$_{7-60}$ alkylaryl ether)$_{1-100}$—CO—NH—(R$_2$ or Ph—R$_2$—Ph)—NH—CO—O—, —R$_1$—NH—CO—NH—(R$_2$ or Ph—R$_2$—Ph)—NH—CO—O—(C$_{1-30}$ alkyl ether or C$_{7-60}$ alkylaryl ether)$_{1-100}$, —R$_1$—NH—CO—NH—(R$_2$ or Ph—R$_2$—Ph)—NH—CO—O—(C$_{1-30}$ alkyl ether or C$_{7-60}$ alkylaryl ether)$_{1-100}$—CO—NH—(R$_2$ or Ph—R$_2$—Ph)—NH—CO—O—, —R$_1$—O—CO—NH—(R$_2$ or Ph—R$_2$—Ph)—NH—CO—NH—(C$_{2-50}$ alkyl amide or C$_{7-70}$ alkylaryl amide)$_{1-100}$, or —R$_1$—NH—CO—NH—(R$_2$ or Ph—R$_2$—Ph)—NH—CO—NH—(C$_{2-50}$ alkyl amide or C$_{8-70}$ alkylaryl amide) 1–100; and C is independently —R— or —R—Ph— in which Ph is p-phenylene.

3. The compound of claim 2, wherein m is 0 and n is 4–16.

4. The compound of claim 2, wherein m is 0–16, n is 0–16, and the sum of m and n is 4–16.

5. The compound of claim 2, wherein m is 0 and n is 2–30.

6. The compound of claim 2, wherein D is independently —SO$_3^-$, —OSO$_3^-$, —PO$_3^-$, —O—PO$_3^{-2}$, —O—PO(O$^-$)—O—PO$_3^{-2}$, —O—PO(O$^-$)—O—PO(O$^-$)O—PO$_3^{-2}$, or —O—PO(O$^-$)—O—CH$_2$—CH$_2$—NH$_3^+$.

7. The compound of claim 6, wherein m is 0 and n is 2–30.

8. The compound of claim 6, wherein m is 0–16, n is 0–16, and the sum of m and n is 4–16.

9. The compound of claim 6, wherein m is 0 and n is 4–16.

10. A compound of the following formula:

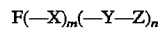

wherein

F is a fullerene core;

each X is independently —CO$_2^-$, —SO$_3^-$, —OH, —SH, —PO$_3^-$, —O—PO$_3^{-2}$, —O—PO(O$^-$)—O—PO$_3^{-2}$, —O—PO(O$^-$)—O—PO(O$^-$)—O—PO$_3^{-2}$, —O—PO(O$^-$)—O—CH$_2$—CH$_2$—NH$_3^+$, —NH$_2$, —NH$_3^+$, —N$^+$H$_2$R$_a$, —N$^+$HR$_a$R$_b$, or —N$^+$R$_a$R$_b$R$_c$;

each Y is —A—B—, in which A is independently —CH$_2$—, —O—, —S—, —NH—CO—NH—, or —NH—CO—; and B is independently —R$_d$—O—[Si(CH$_3$)$_2$—O—]$_{1-100}$, C$_{1-2000}$ alkyl, C$_{6-40}$ aryl, C$_{7-60}$ alkylaryl, C$_{7-60}$ arylalkyl, (C$_{1-30}$ alkyl ether)$_{1-100}$, (C$_{6-40}$ aryl ether)$_{1-100}$, (C$_{7-60}$ alkylaryl ether)$_{1-100}$, (C$_{7-60}$ arylalkyl ether)$_{1-100}$, (C$_{1-30}$ alkyl thioether)$_{1-100}$, (C$_{6-40}$ aryl thioether)$_{1-100}$, (C$_{7-60}$ alkylaryl thioether)$_{1-100}$, (C$_{7-60}$ arylalkyl thioether)$_{1-100}$, (C$_{2-50}$ alkyl ester)$_{1-100}$, (C$_{7-60}$ aryl ester)$_{1-100}$, (C$_{8-70}$ alkylaryl ester)$_{1-100}$, (C$_{8-70}$ arylalkyl ester)$_{1-100}$, —R—CO—O—(C$_{1-30}$ alkyl ether)$_{1-100}$, —R—CO—O—(C$_{6-40}$ aryl ether)$_{1-100}$, —R—CO—O—(C$_{7-60}$ alkylaryl ether)$_{1-100}$, —R—CO—O—(C$_{7-60}$ arylalkyl ether)$_{1-100}$, (C$_{4-50}$ alkyl urethane)$_{1-100}$, (C$_{14-60}$ aryl urethane)$_{1-100}$, (C$_{10-80}$ alkylaryl urethane)$_{1-100}$, (C$_{10-80}$ arylalkyl urethane)$_{1-100}$, (C$_{5-50}$ alkyl urea)$_{1-100}$, (C$_{14-60}$ aryl urea)$_{1-100}$, (C$_{10-80}$ alkylaryl urea)$_{1-100}$, (C$_{10-80}$ arylalkyl urea)$_{1-100}$, (C$_{2-50}$ alkyl amide)$_{1-100}$, (C$_{7-60}$ aryl amide)$_{1-100}$, (C$_{8-70}$ alkylaryl amide)$_{1-100}$, (C$_{8-70}$ arylalkyl amide)$_{1-100}$, (C$_{3-30}$ alkyl anhydride)$_{1-100}$, (C$_{6-60}$ aryl anhydride)$_{1-100}$, (C$_{9-60}$ alkylaryl anhydride)$_{1-100}$, (C$_{9-60}$ arylalkyl anhydride)$_{1-100}$, (C$_{2-30}$ alkyl carbonate)$_{1-100}$, (C$_{7-50}$ aryl carbonate)$_{1-100}$, (C$_{8-60}$ alkylaryl carbonate)$_{1-100}$, (C$_{8-60}$ arylalkyl carbonate)$_{1-100}$, —R$_1$—O—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$, —R$_1$—O—CO—NH—(R$_2$ or Ar—R$_2$—Ar)—NH—CO—O—(C$_{2-50}$ alkyl ester, C$_{7-60}$ aryl ester, C$_{8-70}$ alkylaryl ester, or C$_{8-70}$ arylalkyl ester)$_{1-100}$, —R$_1$—O—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$—CO—NH—(R$_2$ or Ar—R$_2$—Ar)—NH—CO—O—, —R$_1$—O—CO—NH—(R$_2$ or Ar—R$_2$—Ar)—NH—CO—O—(C$_{2-50}$ alkyl ester, C$_{7-60}$ aryl ester, C$_{8-70}$ alkylaryl ester, or C$_{8-70}$ arylalkyl ester)$_{1-100}$—R$_3$—O—CO—NH—(R$_2$ or Ar—R$_2$—Ar)—NH—CO—O—, —R$_1$—NH—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$, —R$_1$—NH—CO—NH—(R$_2$ or Ar—R$_2$—Ar)—NH—CO—O—(C$_{2-50}$ alkyl ester, C$_{7-60}$ aryl ester, C$_{8-70}$ alkylaryl ester, or C$_{8-70}$ arylalkyl ester)$_{1-100}$, —R$_1$—NH—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$—CO—NH—(R$_2$ or Ar—R$_2$—Ar)—NH—CO—O—, —R$_1$—NH—CO—NH—(R$_2$ or Ar—R$_2$—Ar)—NH—CO—O—(C$_{2-50}$ alkyl ester, C$_{7-60}$ aryl ester, C$_{8-70}$ alkylaryl ester, or C$_{8-70}$ arylalkyl ester)$_{1-100}$—R$_3$—O—CO—NH—(R$_2$ or Ar—R$_2$—Ar)—NH—CO—O—, —R$_1$—O—CO—NH—(R$_2$ or Ar—R$_2$—Ar)—NH—CO—NH—(C$_{2-50}$ alkyl amide, C$_{7-60}$ aryl amide, C$_{8-70}$ alkylaryl amide, or C$_{8-70}$ arylalkyl amide)$_{1-100}$, or —R$_1$—NH—CO—NH—(R$_2$ or Ar—R$_2$—Ar)—NH—CO—NH—(C$_{2-50}$ alkyl amide, C$_{7-60}$ aryl amide, C$_{8-70}$ alkylaryl amide, or C$_{8-70}$ arylalkyl amide)$_{1-100}$;

each Z is —C—D, wherein C is independently —R—, —R—Ar—, —Ar—, or —Ar—R—; and D is independently —OH, —SH, —SO$_3^-$, —OSO$_3^-$, —CO$_2^-$, —PO$_3^-$, —O—PO$_3^{-2}$, —O—PO(O$^-$)—O—PO$_3^{-2}$, —O—PO(O$^-$)—O—PO(O$^-$)O—PO$_3^{-2}$, —O—PO(O$^-$)—O—CH$_2$—CH$_2$—NH$_3^+$, —NH$_2$, —NH$_3^+$, —N$^+$H$_2$R$_a$, —N$^+$HR$_a$R$_b$, or —N$^+$R$_a$R$_b$R$_c$; and m is 0–30, n is 1–30, and the sum of m and n is 2–30; in which each of R, R$_1$, R$_2$, R$_3$, R$_a$, R$_b$, R$_c$, R$_d$, R$_{a'}$, R$_{b'}$ and R$_{c'}$ is independently C$_{1-20}$ alkyl, and Ar is independently C$_{6-40}$ aryl.

11. The compound of claim 10, wherein

B is independently —R$_d$—O—[Si(CH$_3$)$_2$—O—]$_{1-100}$, C$_{1-2000}$ alkyl, C$_{6-40}$ aryl, C$_{7-60}$ alkylaryl, C$_{7-60}$ arylalkyl, (C$_{1-30}$ alkyl ether)$_{1-100}$, (C$_{7-60}$ alkylaryl ether)$_{1-100}$, (C$_{1-30}$ alkyl thioether)$_{1-100}$, (C$_{7-60}$ alkylaryl thioether)$_{1-100}$, (C$_{2-50}$ alkyl ester)$_{1-100}$, (C$_{8-70}$ alkylaryl ester)$_{1-100}$, —R—CO—O—(C$_{1-30}$ alkyl ether)$_{1-100}$, —R—CO—O—(C$_{7-60}$ alkylaryl ether)$_{1-100}$, (C$_{4-50}$ alkyl urethane)$_{1-100}$, (C$_{10-80}$ alkylaryl urethane)$_{1-100}$, (C$_{5-50}$ alkyl urea)$_{1-100}$, (C$_{10-80}$ alkylaryl urea)$_{1-100}$, (C$_{2-50}$ alkyl amide)$_{1-100}$, (C$_{8-70}$ alkylaryl amide)$_{1-100}$, (C$_{3-30}$ alkyl anhydride)$_{1-100}$, (C$_{9-60}$ alkylaryl anhydride)$_{1-100}$, (C$_{2-30}$ alkyl carbonate)$_{1-100}$, (C$_{8-60}$ alkylaryl carbonate)$_{1-100}$, —R$_1$—O—CO—NH—(R$_2$ or Ph—R$_2$—Ph)—NH—CO—O—(C$_{1-30}$ alkyl ether or C$_{7-60}$ alkylaryl ether)$_{1-100}$, —R$_1$—O—CO—NH—(R$_2$ or Ph—R$_2$—Ph)—NH—CO—O—(C$_{2-50}$ alkyl ester or C$_{8-70}$ alkylaryl ester)$_{1-100}$, —R$_1$—O—CO—NH—(R$_2$ or Ph—R$_2$—Ph)—NH—CO—O—(C$_{1-30}$ alkyl ether or C$_{7-60}$ alkylaryl ether)$_{-100}$—CO—NH—(R$_2$ or Ph—R$_2$—Ph)—NH—CO—O—, —R$_1$—NH—CO—NH—(R$_2$ or Ph—R$_2$—Ph)—NH—CO—O—(C$_{1-30}$ alkyl ether or C$_{7-60}$ alkylaryl ether)$_{1-100}$, —R$_1$—NH—CO—NH—(R$_2$ or Ph—R$_2$—Ph)—NH—CO—O—(C$_{2-50}$ alkyl ester or C$_{8-70}$ alkylaryl ester)$_{1-100}$, —R$_1$—NH—CO—NH—(R$_2$ or Ph—R$_2$—Ph)—NH—CO—O—(C$_{1-30}$ alkyl ether or C$_{7-60}$ alkylaryl ether)$_{1-100}$—CO—NH—(R$_2$ or Ph—R$_2$—Ph)—NH—CO—O—, —R$_1$—O—CO—NH—(R$_2$ or Ph—R$_2$—Ph)—NH—CO—NH—(C$_{2-50}$ alkyl amide or C$_{7-70}$ alkylaryl amide)$_{1-100}$, or —R$_1$—NH—CO—NH—(R$_2$ or Ph—R$_2$—Ph)—NH—CO—NH—(C$_{2-50}$ alkyl amide or C$_{8-70}$ alkylaryl amide)$_{1-100}$; and C is independently —R— or —R—Ph— in which Ph is p-phenylene.

12. The compound of claim 11, wherein m is 0 and n is 2–30.

13. The compound of claim 11, wherein m is 0–16, n is 1–16, and the sum of m and n is 4–16.

14. The compound of claim 11, wherein D is independently —SO$_3^-$, —OSO$_3^-$, —PO$_3^-$, —O—PO$_3^{-2}$, —O—PO(O$^-$)—O—PO$_3^{-2}$, —O—PO(O$^-$)—O—PO(O$^-$)O—PO$_3^{-2}$, or —O—PO(O$^-$)—O—CH$_2$—CH$_2$—NH$_3^+$.

15. The compound of claim 14, wherein m is 0 and n is 2–30.

16. The compound of claim 14, wherein m is 0–16, n is 1–16, and the sum of m and n is 4–16.

17. A composition comprising a biologically compatible substance and a compound of the following formula:

F(—X)$_m$(—Y—Z)$_n$ wherein

F is a fullerene core;

each X is independently —CO$_2^-$, —SO$_3^-$, —SH, —OH, —PO$_3^-$, —O—PO$_3^{-2}$, —O—PO(O$^-$)—O—PO$_3^{-2}$, —O—PO(O$^-$)—O—PO(O$^-$)—O—PO$_3^{-2}$, —O—PO(O$^-$)—O—CH$_2$—CH$_2$—NH$_3^+$, —NH$_2$, —NH$_3^+$, —N$^+$H$_2$R$_a$, —N$^+$HR$_a$R$_b$, or —N$^+$R$_a$R$_b$R$_c$;

each Y is —A—B—, in which A is independently —CH$_2$—, —O—, —NH—, —S—, —O—CO—, —O—CO—O—, —O—CO—NH—, —NH—CO—NH—, or —NH—CO—; and B is independently—R$_d$—O—[Si(CH$_3$)$_2$—O—]$_{1-100}$, C$_{1-2000}$ alkyl, C$_{6-40}$ aryl, C$_{7-60}$ alkylaryl, C$_{7-60}$ arylalkyl, (C$_{1-30}$ alkyl ether)$_{-100}$, (C$_{6-40}$ aryl ether)$_{1-100}$, (C$_{7-60}$ alkylaryl ether)$_{-100}$, (C$_{7-60}$ arylalkyl ether)$_{1-100}$, (C$_{1-30}$ alkyl thioether)$_{1-100}$, (C$_{6-40}$ aryl thioether)$_{1-100}$, (C$_{7-60}$ alkylaryl thioether)$_{1-100}$, (C$_{7-60}$ arylalkyl thioether)$_{1-100}$, (C$_{2-50}$ alkyl ester)$_{1-100}$, (C$_{7-60}$ aryl ester)$_{1-100}$, (C$_{8-70}$ alkylaryl ester)$_{1-100}$, (C$_{8-70}$ arylalkyl ester)$_{1-100}$, —R—CO—O—($C_{1-30}$ alkyl ether)$_{1-100}$, —R—CO—O—($C_{6-40}$ aryl ether)$_{1-100}$, —R—CO—O—($C_{7-60}$ alkylaryl ether)$_{1-100}$, —R—CO—O—($C_{7-60}$ arylalkyl ether)$_{-100}$, ($C_{4-50}$ alkyl urethane)$_{-100}$, ($C_{14-60}$ aryl urethane)$_{1-100}$, ($C_{10-80}$ alkylaryl urethane)$_{-100}$, ($C_{10-80}$ arylalkyl urethane)$_{1-100}$, ($C_{5-50}$ alkyl urea)$_{-100}$, ($C_{14-60}$ aryl urea)$_{1-100}$, ($C_{10-80}$ alkylaryl urea)$_{1-100}$, ($C_{10-80}$ arylalkyl urea)$_{-100}$, ($C_{2-50}$ alkyl amide)$_{1-100}$, ($C_{7-60}$ aryl amide)$_{1-100}$, ($C_{8-70}$ alkylaryl amide)$_{1-100}$, ($C_{8-70}$ arylalkyl amide)$_{1-100}$, ($C_{3-30}$ alkyl anhydride)$_{1-100}$, ($C_{8-50}$ aryl anhydride)$_{1-100}$, ($C_{9-60}$ alkylaryl anhydride)$_{1-100}$, ($C_{9-60}$ arylalkyl anhydride)$_{1-100}$, ($C_{2-30}$ alkyl carbonate)$_{-100}$, ($C_{7-50}$ aryl carbonate) 1–100, ($C_{8-60}$ alkylaryl carbonate)$_{1-100}$, ($C_{8-60}$ arylalkyl carbonate)$_{1-100}$, —$R_1$—O—CO—NH—($R_2$ or Ar—$R_2$—Ar)—NH—CO—O—($C_{1-30}$ alkyl ether, $C_{6-40}$ aryl ether, $C_{7-60}$ alkylaryl ether, or $C_{7-60}$ arylalkyl ether)$_{1-100}$, —$R_1$—O—CO—NH—($R_2$ or Ar—$R_2$—Ar)—NH—CO—O—($C_{2-50}$ alkyl ester, $C_{7-60}$ aryl ester, $C_{8-70}$ alkylaryl ester, or $C_{8-70}$ arylalkyl ester)$_{-100}$, —$R_1$—O—CO—NH—($R_2$ or Ar—$R_2$—Ar) —NH—CO—O—($C_{1-30}$ alkyl ether, $C_{6-40}$ aryl ether, $C_{7-60}$ alkylaryl ether, or $C_{7-60}$ arylalkyl ether)$_{-100}$— CO—NH—($R_2$ or Ar—$R_2$—Ar)—NH—CO—O—, —$R_1$—O—CO—NH—($R_2$ or Ar—$R_2$—Ar)—NH— CO—O—($C_{2-50}$ alkyl ester, $C_{7-60}$ aryl ester, $C_{8-70}$ alkylaryl ester, or $C_{8-70}$ arylalkyl ester)$_{-100}$—$R_3$—O— CO—NH—($R_2$ or Ar—$R_2$—Ar)—NH—CO—O—, —$R_1$—NH—CO—NH—($R_2$ or Ar—$R_2$—Ar)—NH— CO—O—($C_{1-30}$ alkyl ether, $C_{6-40}$ aryl ether, $C_{7-60}$ alkylaryl ether, or $C_{7-60}$ arylalkyl ether)$_{-100}$, —$R_1$— NH—CO—NH—($R_2$ or Ar—$R_2$—Ar)—NH—CO— O—($C_{2-50}$ alkyl ester, $C_{7-60}$ aryl ester, $C_{8-70}$ alkylaryl ester, or $C_{8-70}$ arylalkyl ester)$_{-100}$, —$R_1$—NH—CO— NH—($R_2$ or Ar—$R_2$—Ar)—NH—CO—O—($C_{1-30}$ alkyl ether, $C_{6-40}$ aryl ether, $C_{7-60}$ alkylaryl ether, or $C_{7-60}$ arylalkyl ether)$_{-100}$—CO—NH—($R_2$ or Ar—$R_2$—Ar)—NH—CO—O—, —$R_1$—NH—CO— NH—($R_2$ or Ar—$R_2$—Ar)—NH—CO—O—($C_{2-50}$ alkyl ester, $C_{7-60}$ aryl ester, $C_{8-70}$ alkylaryl ester, or $C_{8-70}$ arylalkyl ester)$_{1-100}$—$R_3$—O—CO—NH—($R_2$ or Ar—$R_2$—Ar)—NH—CO—O—, —$R_1$—O—CO— NH—($R_2$ or Ar—$R_2$—Ar)—NH—CO—NH—($C_{2-50}$ alkyl amide, $C_{7-60}$ aryl amide, $C_{8-70}$ alkylaryl amide, or $C_{8-70}$ arylalkyl amide)$_{-100}$, or —$R_1$—NH—CO— NH—($R_2$ or Ar—$R_2$—Ar)—NH—CO—NH—($C_{2-50}$ alkyl amide, $C_{7-60}$ aryl amide, $C_{8-70}$ alkylaryl amide, or $C_{8-70}$ arylalkyl amide)$_{-100}$;

each Z is —C—D, wherein C is independently —R—, —R—Ar—, —Ar—, or —Ar—R—; and D is independently —H, —OH, —SH, —$SO_3^-$, —$OSO_3^-$, —$CO_2^-$, —$PO_3^-$, —O—$PO_3^{-2}$, —O—PO($O^-$)—O— $PO_3^{-2}$, —O—PO($O^-$)—O—PO($O^-$)O—$PO_3^{-2}$, O—PO($O^-$)—O—$CH_2$—$CH_2$—$NH_3^+$, —$NH_2$, —$NH_3^+$, —$N^+H_2R_a$·, —$N^+HR_aR_b$·, or —$N^+R_aR_bR_c$·; and m is 0–30, n is 0–30, and the sum of m and n is 2–30;

in which each of R, $R_1$, $R_2$, $R_3$, $R_a$, $R_b$, $R_c$, $R_d$, $R_{a'}$, $R_{b'}$, and $R_{c'}$, is independently $C_{1-20}$ alkyl, and Ar is independently $C_{6-40}$ aryl.

18. The composition of claim 17, wherein

B is independently —$R_d$—O—[Si($CH_3$)$_2$—O—]$_{1-100}$, $C_{1-2000}$ alkyl, $C_{6-40}$ aryl, $C_{7-60}$ alkylaryl, $C_{7-60}$ arylalkyl, ($C_{1-30}$ alkyl ether)$_{1-100}$, ($C_{7-60}$ alkylaryl ether)$_{1-100}$, ($C_{1-30}$ alkyl thioether)$_{1-100}$, ($C_{7-60}$ alkylaryl thioether)$_{1-100}$, ($C_{2-50}$ alkyl ester)$_{1-100}$, ($C_{8-70}$ alkylaryl ester)$_{1-100}$, —R—CO—O—($C_{1-30}$ alkyl ether)$_{1-100}$, —R—CO—O—($C_{7-60}$ alkylaryl ether)$_{1-100}$, ($C_{4-50}$ alkyl urethane)$_{1-100}$, ($C_{10-80}$ alkylaryl urethane)$_{1-100}$, ($C_{5-50}$ alkyl urea)$_{1-100}$, ($C_{10-80}$ alkylaryl urea)$_{1-100}$, ($C_{2-50}$ alkyl amide)$_{1-100}$, ($C_{8-70}$ alkylaryl amide)$_{1-100}$, ($C_{3-30}$ alkyl anhydride)$_{1-100}$, ($C_{9-60}$ alkylaryl anhydride)$_{1-100}$, ($C_{2-30}$ alkyl carbonate)$_{1-100}$, ($C_{8-60}$ alkylaryl carbonate)$_{1-100}$, —$R_1$—O—CO— NH—($R_2$ or Ph—$R_2$—Ph)—NH—CO—O—($C_{1-30}$ alkyl ether or $C_{7-60}$ alkylaryl ether)$_{1-100}$, —$R_1$—O— CO—NH—($R_2$ or Ph—$R_2$—Ph)—NH—CO—O— ($C_{2-50}$ alkyl ester or $C_{8-70}$ alkylaryl ester)$_{1-100}$, —$R_1$— O—CO—NH—($R_2$ or Ph—$R_2$—Ph)—NH—CO— O—($C_{1-30}$ alkyl ether or $C_{7-60}$ alkylaryl ether)$_{1-100}$— CO—NH—($R_2$ or Ph—$R_2$—Ph)—NH—CO—O—, —$R_1$—NH—CO—NH—($R_2$ or Ph—$R_2$—Ph)—NH— CO—O—($C_{1-30}$ alkyl ether or $C_{7-60}$ alkylaryl ether)$_{1-100}$, —$R_1$—NH—CO—NH—($R_2$ or Ph—$R_2$— Ph)—NH—CO—O—($C_{2-50}$ alkyl ester or $C_{8-70}$ alkylaryl ester)$_{1-100}$, —$R_1$—NH—CO—NH—($R_2$ or Ph—$R_2$—Ph)—NH—CO—O—($C_{1-30}$ alkyl ether or $C_{7-60}$ alkylaryl ether)$_{1-100}$—CO—NH—($R_2$ or Ph—$R_2$—Ph)—NH—CO—O—, —$R_1$—O—CO— NH—($R_2$ or Ph—$R_2$—Ph)—NH—CO—NH—($C_{2-50}$ alkyl amide or $C_{7-70}$ alkylaryl amide)$_{1-100}$, or —$R_1$— NH—CO—NH—($R_2$ or Ph—$R_2$—Ph)—NH—CO— NH—($C_{2-50}$ alkyl amide or $C_{8-70}$ alkylaryl amide)$_{1-100}$; and C is independently —R— or —R—Ph— in which Ph is p-phenylene.

19. The composition of claim 18, wherein each X is independently —$CO_2^-$, —$SO_3^-$, —$PO_3^-$, —O—$PO_3^{-2}$, —O—PO($O^-$)—O—$PO_3^{-2}$, or —O—PO($O^-$)—O—PO ($O^-$)—O—$PO_3^{-2}$, —O—PO($O^-$)—O—$CH_2$—$CH_2$— $NH_3^+$.

20. The composition of claim 19, wherein m is 0–16, n is 1–16, and the sum of m and n is 4–16.

* * * * *